United States Patent
Bresolin et al.

(10) Patent No.: US 10,359,614 B2
(45) Date of Patent: *Jul. 23, 2019

(54) DIAGNOSTIC APPARATUS

(71) Applicant: ADVANCED ANIMAL DIAGNOSTICS, INC., Durham, NC (US)

(72) Inventors: Stefano Bresolin, Garner, NC (US); David A. Calderwood, Chapel Hill, NC (US); Tobias M. Heineck, Durham, NC (US); David Newcomb, Morrisville, NC (US); Chris Paul, Hillsborough, NC (US); Jasper N. Pollard, Durham, NC (US); Rodolfo R. Rodriguez, Cary, NC (US); Demetris Young, Durham, NC (US)

(73) Assignee: Advanced Animal Diagnostics, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/239,208

(22) PCT Filed: Jul. 2, 2013

(86) PCT No.: PCT/US2013/049112
§ 371 (c)(1),
(2) Date: Feb. 17, 2014

(87) PCT Pub. No.: WO2014/008282
PCT Pub. Date: Jan. 9, 2014

(65) Prior Publication Data
US 2014/0233098 A1 Aug. 21, 2014

Related U.S. Application Data

(63) Continuation-in-part of application No. 13/928,741, filed on Jun. 27, 2013, now Pat. No. 9,816,982.
(Continued)

(51) Int. Cl.
*G02B 21/26* (2006.01)
*G01N 33/487* (2006.01)
(Continued)

(52) U.S. Cl.
CPC ....... *G02B 21/26* (2013.01); *G01N 33/48785* (2013.01); *G02B 21/0016* (2013.01); *G06F 1/20* (2013.01); *G02B 21/28* (2013.01)

(58) Field of Classification Search
CPC .... G02B 21/00; G02B 21/0016; G02B 21/28; G02B 21/26; G02B 21/34; G02B 21/006;
(Continued)

(56) References Cited

U.S. PATENT DOCUMENTS 4,440,301 A  4/1984 Intengan
4,698,262 A  10/1987 Schwartz et al.
(Continued)

FOREIGN PATENT DOCUMENTS

EP  1 975 618 A1  10/2008
JP  2011-004654 A  1/2011
(Continued)

OTHER PUBLICATIONS

Anderson et al. "Fresh cow mastitis monitoring on day 3 postpartum and its relationship to subsequent milk production", *Journal of Dairy Science*, Dec. 2010, vol. 93, No. 12, 5673-5683.
(Continued)

*Primary Examiner* — Mustak Choudhury
(74) *Attorney, Agent, or Firm* — Myers Bigel, P.A.

(57) ABSTRACT

An automated microscope apparatus comprises an outer housing having an external wall; optionally but preferably an internal wall in the housing configured to form a first compartment and a separate second compartment in the outer housing; a microscope assembly in the housing (preferably in the first compartment); a microprocessor in the housing (preferably in the second compartment), and (optionally but preferably) a heat sink mounted on the housing external wall, preferably adjacent the second compartment, with the microprocessor thermally coupled to said heat sink and operatively associated with the microscope assembly. Systems and methods employing the same are also described, along with component parts thereof.

10 Claims, 19 Drawing Sheets

Related U.S. Application Data

(60) Provisional application No. 61/667,691, filed on Jul. 3, 2012.

(51) Int. Cl.
   *G02B 21/00* (2006.01)
   *G06F 1/20* (2006.01)
   *G02B 21/28* (2006.01)

(58) Field of Classification Search
   CPC ........ G02B 21/06; G02B 21/16; G02B 21/24; G02B 21/125; G02B 21/365; G06F 1/20; G01N 33/48785; C12M 41/14; C12M 41/18; C12M 41/36; C12M 41/48; C12M 23/42; C12M 23/58; C12M 29/26
   USPC ....... 359/391–393, 395, 368, 377, 382, 656; 355/53, 72, 75; 382/128
   See application file for complete search history.

(56) References Cited

U.S. PATENT DOCUMENTS

| | | | |
|---|---|---|---|
| 4,946,266 A | 8/1990 | Kraft et al. | |
| 5,132,210 A | 7/1992 | Adams et al. | |
| 5,932,872 A | 8/1999 | Price | |
| 6,057,166 A | 5/2000 | Childs et al. | |
| 6,248,596 B1 | 6/2001 | Durst et al. | |
| 6,322,963 B1 | 11/2001 | Bauer | |
| 6,627,621 B2 | 9/2003 | Nagaoka et al. | |
| 6,750,006 B2 | 6/2004 | Powers et al. | |
| 6,790,661 B1 | 9/2004 | Goodnow | |
| 7,141,773 B2 | 11/2006 | Kaplan et al. | |
| 7,390,997 B2 | 6/2008 | Tohma | |
| 7,566,533 B2 | 7/2009 | Jacobs et al. | |
| 7,589,962 B1 | 9/2009 | Bhatia | |
| 7,855,051 B2 | 12/2010 | Anderson et al. | |
| 7,861,768 B1* | 1/2011 | Ghantiwala | F28D 15/0275 165/104.21 |
| 7,898,673 B2 | 3/2011 | Randers-Pehrson et al. | |
| 7,932,093 B2 | 4/2011 | Renuart et al. | |
| 7,943,153 B1 | 5/2011 | Leonard et al. | |
| 8,014,583 B2 | 9/2011 | Zahniser | |
| 8,021,848 B2 | 9/2011 | Straus | |
| 8,067,246 B2 | 11/2011 | Marlborough et al. | |
| 2001/0036645 A1 | 11/2001 | McNeirney et al. | |
| 2002/0098588 A1 | 7/2002 | Sammak et al. | |
| 2002/0169394 A1 | 11/2002 | Eppstein et al. | |
| 2003/0127609 A1 | 7/2003 | El-Hage et al. | |
| 2003/0206296 A1 | 11/2003 | Wolleschensky et al. | |
| 2004/0101826 A1 | 5/2004 | Jones et al. | |
| 2004/0101912 A1 | 5/2004 | Rubin et al. | |
| 2004/0115624 A1 | 6/2004 | Wolde-Mariam | |
| 2004/0208350 A1* | 10/2004 | Rea | G01M 11/00 382/128 |
| 2004/0223132 A1* | 11/2004 | Nishi | G03F 7/70741 355/75 |
| 2005/0260695 A1 | 11/2005 | Fleming et al. | |
| 2006/0068412 A1 | 3/2006 | Tang et al. | |
| 2006/0134796 A1 | 6/2006 | Bommarito et al. | |
| 2007/0015151 A1 | 1/2007 | Schrenzel et al. | |
| 2007/0190566 A1 | 8/2007 | Montagu | |
| 2007/0242349 A1* | 10/2007 | Tafas | B01L 9/52 359/391 |
| 2007/0287147 A1 | 12/2007 | Nagamune et al. | |
| 2008/0088918 A1 | 4/2008 | O'Connell | |
| 2008/0220539 A1 | 9/2008 | Brauner et al. | |
| 2008/0259566 A1 | 10/2008 | Fried | |
| 2009/0042814 A1 | 2/2009 | Petyaev et al. | |
| 2009/0068759 A1 | 3/2009 | Arenas et al. | |
| 2009/0116101 A1* | 5/2009 | Tafas | G02B 21/24 359/369 |
| 2009/0233329 A1 | 9/2009 | Rodriguez et al. | |
| 2010/0118394 A1 | 5/2010 | Hecker | |
| 2010/0135861 A1 | 6/2010 | Sage et al. | |
| 2010/0210022 A1 | 8/2010 | Madura | |
| 2010/0227333 A1 | 9/2010 | Horowitz | |
| 2010/0254854 A1 | 10/2010 | Rich et al. | |
| 2010/0255601 A1 | 10/2010 | Beaudet et al. | |
| 2010/0279310 A1 | 11/2010 | Sia et al. | |
| 2010/0328766 A1 | 12/2010 | Griffin et al. | |
| 2011/0003310 A1 | 1/2011 | Ennis et al. | |
| 2011/0090326 A1 | 4/2011 | Kenny et al. | |
| 2011/0117025 A1 | 5/2011 | Dacosta et al. | |
| 2012/0082361 A1 | 4/2012 | Burke et al. | |

FOREIGN PATENT DOCUMENTS

| | | |
|---|---|---|
| WO | WO 2004/094977 A2 | 11/2004 |
| WO | WO 2004/097412 | 11/2004 |
| WO | WO 2008/002563 A2 | 1/2008 |
| WO | WO 2008/021862 | 2/2008 |
| WO | WO 2009/013683 | 1/2009 |
| WO | WO 2009/105711 | 8/2009 |
| WO | WO 2010/013335 A1 | 2/2010 |
| WO | WO 2012/051372 | 4/2012 |
| WO | WO 2012/094625 | 7/2012 |

OTHER PUBLICATIONS

Ball et al. "An Antigen Capture ELISA Test using Monoclonal Antibodies for the Detection of Mycoplasma californicum in Milk", *Veterinary Immunology and Immunopathology*, 1990, vol. 25, 269-278.

Boothby et al. "Detecting Mycoplasma bovis in milk by enzyme-linked immunosorbent assay, using monoclonal antibodies", *American Journal of Veterinary Research*, 1986, 47(5)1082-1084.

Cimolai et al. "Culture-amplified Immunological Detection of Mycoplasma pneumoniae in Clinical Specimens", *Diagn Microbiol Infect Dis.*, 1988;9:207-212.

Fedorko et al. "Evaluation of a Rapid Enzyme Immunoassay System for Serologic Diagnosis of Mycoplasma pneumoniae Infection", *Diagn Microbiol Infect Dis.*, 1995;23:85-88.

Heller et al. "Antigen capture ELISA using a monoclonal antibody for the detection of Mycoplasma bovis in milk", *Veterinary Microbiology*, 1993, 37:127-133.

Kok et al. "Routine diagnosis of seven respiratory viruses and Mycoplasma pneumoniae by enzyme immunoassay", *Journal of Virological Methods*, 1994, 50:87-100.

Madsen et al. "The simultaneous direct detection of Mycoplasma pneumoniae and Legionella pneumophila antigens in sputum specimens by a monoclonal antibody immunoblot assay", *Journal of Immunological Methods*, 1987, 103:205-210.

Martinez et al. "Immunobinding Assay for Detection of Mycoplasma bovis in Milk", *Can J Vet Res*, 1990; 54:251-255.

Miettinen et al. Detection of Mycoplasma hominis Antigen in Clinical Specimens by Using a Four-Layer Modification of Enzyme Immunoassay (EIA), *Journal of Immunological Methods*, 1984, 69:267-275.

(56) References Cited

OTHER PUBLICATIONS

Talkington et al. "Analysis of Eight Commercial Enzyme Immunoassay Tests for Detection of Antibodies to Mycoplasma pneumoniae in Human Serum" *Clin. Diagn. Lab. Immunol.*, 2004, 11(5):862.

Tuuminen et al. "Improved sensitivity and specificity of enzyme immunoassays with P1-adhesin enriched antigen to detect acute Mycoplasma pneumoniae infection", *Journal of Microbiological Methods*, 2001, 44:27-37.

Uldum et al. "Enzyme Immunoassay for Detection of Immunoglobulin M (IgM) and IgG Antibodies to Mycoplasma pneumoniae", *Journal of Clinical Microbiology*, May 1992, vol. 30, No. 5, pp. 1198-1204.

Elert et al. Diameter of a Yeast, The Physics Factbook, 2000, Retrieved from the internet on Nov. 22, 2013 at URL http://hypertextbook.com/facts/2000/JennyNg.shtml.

Fischer J.E. et al. "Autofokus zur schnellen Verarbeitung mikroskipischer Praeparate", Informatik Fachberichte—Mustererkennung 1991, 13, DAGM Symposium Proceedings, Munchen, Oktober 9-11, 19991, vol. 290, Oct. 9, 1991, pp. 367-372.

Geusebroek et al. "Robust autofocusing in microscopy", Cytometry, vol. 39, Feb. 2000, pp. 1-9.

International Search Report and Written Opinion Corresponding to International Application No. PCT/US2013/049112; dated Dec. 13, 2013; 12 Pages.

International Search Report and Written Opinion Corresponding to International Application No. PCT/US2013/049247; dated Dec. 5, 2013; 13 Pages.

International Search Report and Written Opinion Corresponding to International Application PCT/US2013/040372; dated Jul. 16, 2013; 9 Pages.

International Search Report and Written Opinion Corresponding to International Application No. PCT/US2013/040379; dated Sep. 5, 2013; 14 Pages.

International Search Report and Written Opinion Corresponding to International Application No. PCT/US2013/040382; dated Dec. 6, 2013; 17 Pages.

Molecular Devices, Multi Dimensional Acquisition: Auto Focus Dialog, Molecular Devices Article #T20125, Aug. 27, 2009, Retrieved from the internet on Nov. 22, 2013 at URL http://support.meta.moleculardevices.com/docs/t20125.pdf.

Supplementary European Search and Opinion, EP 13813619, dated Nov. 30, 2015.

\* cited by examiner

DIAGNOSTIC APPARATUS

RELATED APPLICATIONS

This application is a 35 U.S.C. § 371 national phase entry of PCT Application PCT/US2013/049112, filed Jul. 2, 2013, and published in English on Jan. 9, 2014, as International Publication No. WO 2014/008282, which is a continuation application of U.S. patent application Ser. No. 13/928,741, filed Jun. 27, 2013, and which claims the benefit of U.S. Provisional Patent Application Ser. No. 61/667,691, filed Jul. 3, 2012, the disclosures of which are incorporated by reference herein in their entirety.

FIELD OF THE INVENTION

The present invention concerns diagnostic methods and apparatus, particularly methods and apparatus useful for detecting white blood cells or analytes in bodily fluids of production animals (for example, bovine mastitis in cattle from milk).

BACKGROUND OF THE INVENTION

Mastitis is the inflammation of the mammary gland caused by microorganisms that invade one or more quadrants of the bovine udder, multiply, and produce toxins that are harmful to the mammary gland. Economic loss to mastitis in the United States is estimated to be over 2 billion dollars. This is approximately 10% of the total value of farm milk sales, and about two-thirds of this loss is due to reduced milk production in subclinically infected cows.

In subclinical mastitis, there may be no visible signs of the disease, and diagnosis of subclinical mastitis may be performed by a somatic cell count (SCC) of the milk. The SCC is the number of leukocytes or white blood cells per volume of milk and is also used as an index of milk quality. It has also been recognized that there are multiple types of leukocytes, each with its own significance. In milk from a healthy animal, the predominant cell types are lymphocytes, followed by much lesser numbers of neutrophils and macrophages. The percentages of each kind of cell rise and fall as part of the immune response to infection. Those percentages, "the differential milk leukocyte count", represent the unique immune status of an individual quarter udder, at a specific point in time for better diagnosis of subclinical mastitis.

One method for detecting the differential milk leukocyte count is using flow-cytometry, which is an expensive, sophisticated tool typically only found in top research laboratories and generally not practical for the farmer. Another method for detecting the differential milk leukocyte count is the "manual milk differential smear" (MMDS), which is a difficult and time consuming procedure, and is subject to great variability, even when performed by highly trained laboratory technologists. Both flow-cytometry and MMDS present practical difficulties for field research or a barn environment.

U.S. Patent Application Publication No. 2009/0233329 to Rodriguez discloses a wedge microfluidic slide chamber for detecting mastitis or other diseases from a body fluid of a mammal, such as from cow's milk. While manual and automated procedures for carrying out disease detection with the aid of such a sample cartridge are described, again there is not described a system and apparatus useful for implementing such procedures in a field or barn environment.

SUMMARY OF THE INVENTION

A first aspect of the invention is an automated microscope apparatus, comprising: an outer housing having an external wall; optionally but preferably an internal wall in said housing, and configured to form a first compartment and a separate second compartment in said outer housing; a microscope assembly in said housing, preferably in said first compartment; and a microprocessor in said housing, preferably in said second compartment; and optionally but preferably a heat sink mounted on said housing external wall, preferably adjacent said second compartment, with said microprocessor thermally coupled to said heat sink and operatively associated with said microscope assembly.

In some embodiments, the microscope assembly comprises: a support frame; a subframe; a plurality of vibration isolators connecting said support frame to said subframe; an XYZ stage connected to said subframe; and an optical stage connected to said subframe. An XYZ drive assembly interconnecting said XYZ stage to said subframe is preferably included.

In some embodiments, the microprocessor is included as a passively cooled microprocessor assembly, comprising: a heat sink having a front surface and back surface; a circuit board having a front surface and back surface, with said microprocessor mounted on said circuit board front surface; a thermal coupler positioned between said microprocessor and said heat sink back surface, said thermal coupler fixed to and in thermal contact with said heat sink back surface; a clamp connected to said thermal coupler and configured to clamp said microprocessor to said thermal coupler, thereby placing said microprocessor, said thermal coupler, and said heat sink in thermal contact with one another.

In some embodiments, the XYZ stage is for securing a sample cartridge in the automated microscope having X, Y, and Z planes of movement, the sample cartridge having an end portion, a pair of generally parallel opposing side edge portions, and a locking edge portion formed thereon. The XYZ stage comprises a base member having a planar stage surface portion; a pair of generally parallel oppositely facing guide members on said planar stage surface and configured for slideably receiving said sample cartridge therebetween; and a locking member on said planar stage surface portion and positioned to press against the sample cartridge locking edge portion when said sample cartridge is inserted between said guide members, so that pressure is exerted by said lock member through said sample cartridge against at least one of said guide members, whereby the cartridge is removably locked in place on the XYZ stage in the Z plane.

A further aspect of the invention is an automated system for detecting a disorder in a subject, comprising: an XYZ stage configured to secure a sample cartridge; said sample cartridge comprising at least one chamber, said at least one chamber containing a biological sample collected from a subject; an imaging system operatively associated with said XYZ stage and configured to image selected cells in said sample, said selected cells including at least neutrophils; an autofocusing system operatively associated with said imaging system and said XYZ stage and configured to focus said imaging system on said at least one chamber; a processor running a software program or other suitable means for generating a count of at least neutrophils in said sample as an aid to detecting a disorder in said subject. In some embodiments, where the cartridge contains multiple chambers, the system may include a controller configured to optionally repeat at least said imaging for at least one additional chamber on said cartridge, as discussed further below.

A further aspect of the invention is a method of automatically focusing a microscope on a specimen by capturing an image from each of a plurality of focal planes in or on said specimen, calculating a focus score for each of said images, selecting the focal plane corresponding to the image having the best focus score, and then repositioning said specimen relative to said microscope so that said microscope is focused on said selected focal plane, characterized by including a plurality of exogenous targets in or on said specimen.

A further aspect of the invention is an automated microscope comprising a specimen support stage, an objective lens, a camera, at least one drive assembly operatively associated with said support stage and/or said objective lens, all of which may be as described herein, and further characterized by a controller operatively associated with said at least one drive assembly for carrying out an autofocus method as described herein.

The foregoing and other objects and aspects of the present invention are described in greater detail below. The disclosures of all US Patent references cited herein are to be incorporated herein by reference.

BRIEF DESCRIPTION OF THE DRAWINGS

FIG. 20 illustrates the display of a user interface of an apparatus of FIG. 2 for input of animal data or information, particularly the type of sample collected, and the number of chambers in the sample cartridge for which sample imaging and analysis is to be carried out;

FIG. 21 illustrates the display of a user interface of an apparatus of FIG. 2 after homing and/or information entry is completed and when the apparatus is ready to receive the sample cartridge.

DETAILED DESCRIPTION OF ILLUSTRATIVE EMBODIMENTS

Figure 1:
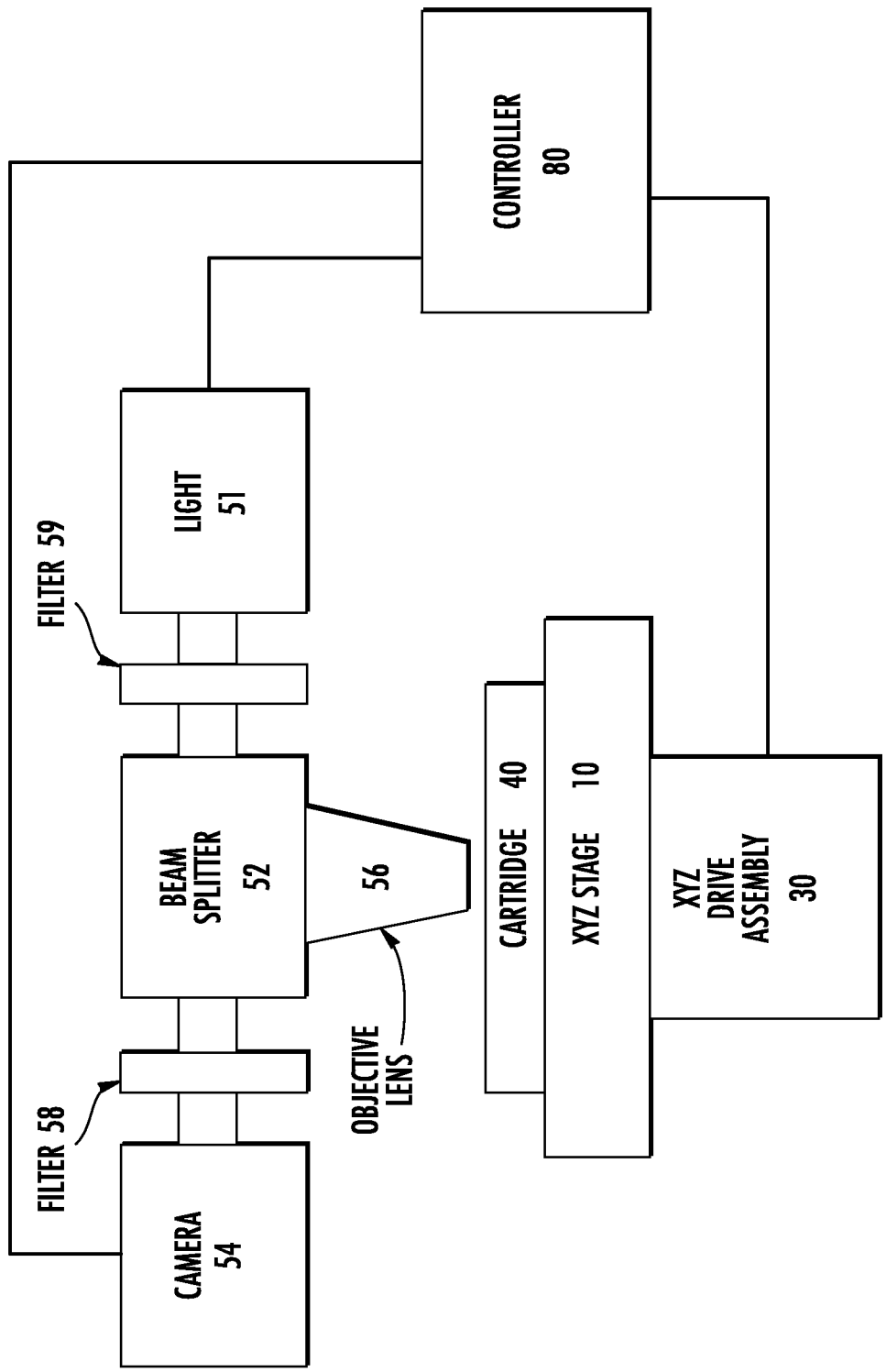
FIG. 1 is a partial schematic diagram of an apparatus of the present invention.

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

"Subject" as used herein includes both human and animal subjects for veterinary purposes, as well as plants for agricultural purposes. Examples of animal subjects include, but are not limited to, mammalian subjects such as dog, cat, cow, sheep, goat, llama, alpaca, camel, horse, pig, chicken, and turkey subjects.

Dairy animals such as cows, goats, sheep, buffalo, and camel, for the production of milk are particularly preferred for some embodiments of the invention.

"Milk" as used herein generally refers to mammalian milk of any species (e.g., cow, goat, human, etc.). The milk is typically raw milk, and is typically raw milk produced by dairy cattle. In some embodiments "milk" includes colostrum; in other embodiments "milk" refers to milk intended for human consumption after the production of colostrum has ceased. The milk may optionally be diluted (typically with an aqueous diluent such as distilled water, saline solution, or buffer solution).

"Colostrum" as used herein is a form of milk produced by mammals in the first few days after birth, that may be higher in antibodies (for imparting passive immunity to offspring).

"Secretions" as used herein is a form of milk produced by mammals just prior to giving birth. Such secretions are sometimes also referred to as "colostrum" but in the present application "secretions" refers to the type of milk produced prior to the subject giving birth, while colostrum refers to the type of milk produced just after the subject giving birth.

"Sample cartridge" or "diagnostic cartridge" as used herein may be any suitable cartridge for containing a cell sample, including but are not limited to cartridges suitable for differential leukocyte analysis as described In R. Rodriguez and C. Galanaugh, US Patent Application Publication No. 2009/0233329 (published Sep. 17, 2009), the disclosure of which is incorporated herein by reference in its entirety, and optionally incorporating the modifications or features discussed further below. In general, and as illustrated further below, such as cartridge includes at least one (e.g., two, four) sample chambers (e.g., a microfluidic chamber), which chamber or chambers may contain suitable cell or leukocyte observation colorants, stains, or reagents (e.g., reagents suitable for visualizing the cells under epifluorescent microscopy). The sample chambers are preferably aligned with one another on the cartridge (that is, on substantially the same Z plane as one another on the cartridge). In a preferred embodiment, each chamber contains reagents for separately and distinctly imaging or detecting neutrophils (or "polymorphonuclear leukocytes" (PMN)), lymphocytes, and macrophages, for differential leukocyte count diagnosis of infections such as bovine mastitis, in accordance with procedures known in the art, or which will be apparent to those skilled in the art based upon the instant disclosure, as discussed further below.

A partial schematic diagram of an apparatus of the present invention is given as an overview in FIG. 1. The apparatus comprises an XYZ stage (10) mounted on an XYZ drive assembly (30). A sample cartridge (40) is removably inserted into or engaged by the XYZ stage. The optical components for carrying out epifluorescent microscopy include a light or light source (51), a beam splitter (52), a camera (54), and an objective lens (56), all configured so that light from the source is directed onto the sample cartridge, and light emitted or fluoresced from the sample cartridge is directed to the camera. Filters (58, 59) are provided between the camera and beam splitter, and between the light source and beam splitter, so that the appropriate wavelengths of light are directed onto the sample cartridge, and the appropriate wavelengths of light are directed onto the camera. All components including the camera, light, and XYZ drive assembly, are controlled by any suitable controller (80), which may comprise a computer or microprocessor with associated memory units, power, and additional control boards (not always shown) such as an XYZ controller board.

Individual components of the methods and apparatus described herein may be as known in the art, or variations thereof that will be apparent to those skilled in the art based on the instant disclosure and prior automated microscopy apparatus such as described in U.S. Pat. No. 4,998,284 to Bacus; U.S. Pat. No. 5,548,661 to Price; U.S. Pat. No. 5,790,710 to Price; U.S. Pat. No. 6,381,058 to Ramm; U.S. Pat. No. 6,929,953 to Wardlaw; U.S. Pat. No. 6,927,903 to Stuckey; U.S. Pat. No. 8,000,511 to Perz; U.S. Pat. No. 8,045,165 to Wardlaw; U.S. Pat. No. 8,081,303 to Levine; or US Patent Application No. 2001/0041347 to Sammak.

Figure 2:
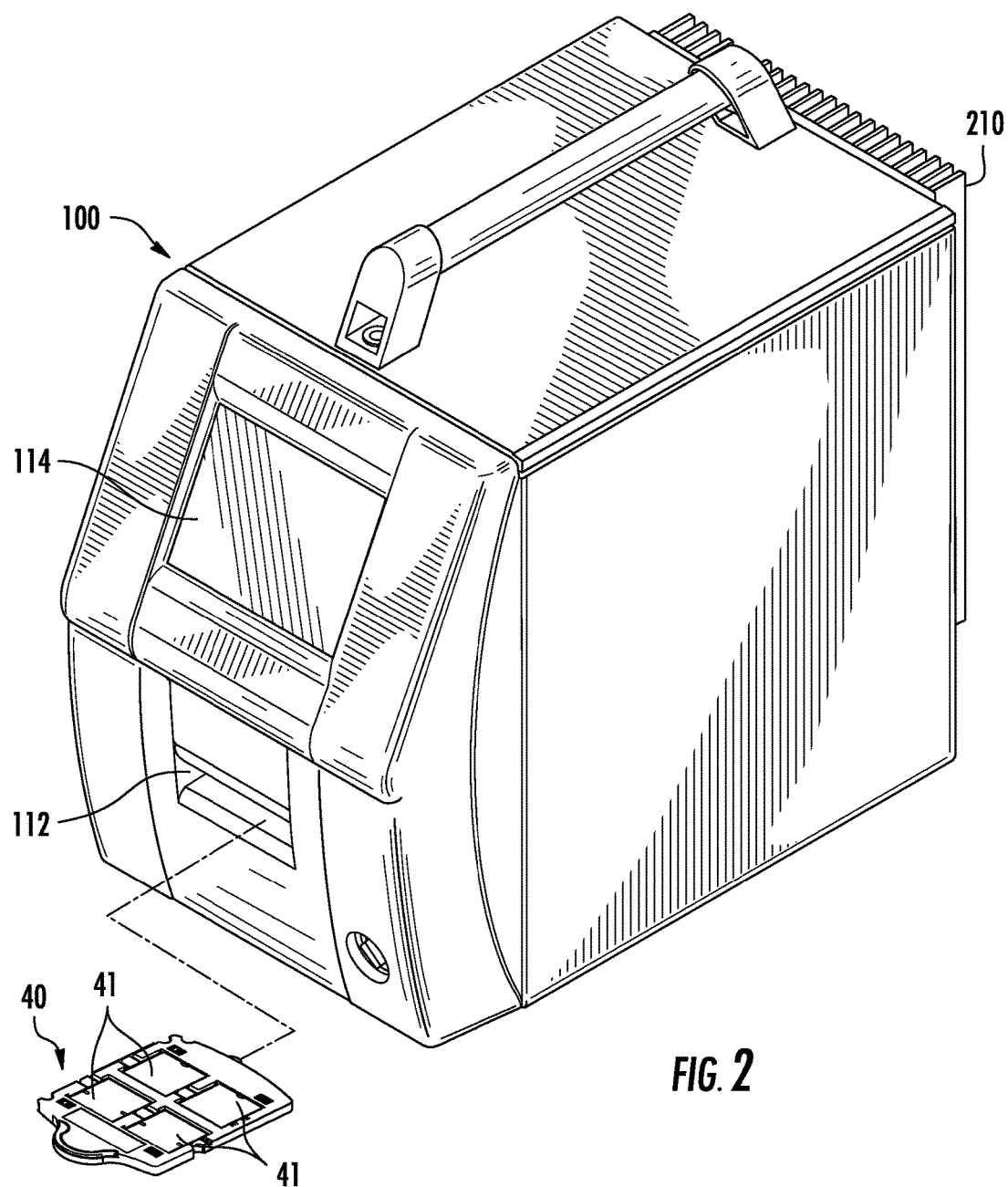
FIG. 2 is a perspective view of an apparatus of the present invention, with a sample cartridge to be inserted and touch screen user interface for input of information and display of results.

FIG. 2 is a perspective view of an apparatus (100) of the present invention, as constructed for portability and use in a dusty or otherwise harsh environment such as a barn or farm, or out-of-doors where animals to be diagnosed are found. All components of FIG. 1 above (and FIG. 3 below) are contained within the housing, except for the sample cartridge, which is removably inserted through a suitable opening (112) in the housing. A touch screen display (114) on the front of the device (e.g., an ESTECOM 6.5 inch intelligent panel LCD display/monitor) is provided to both display results and control the apparatus through its operational steps, as discussed further below.

Figure 3:
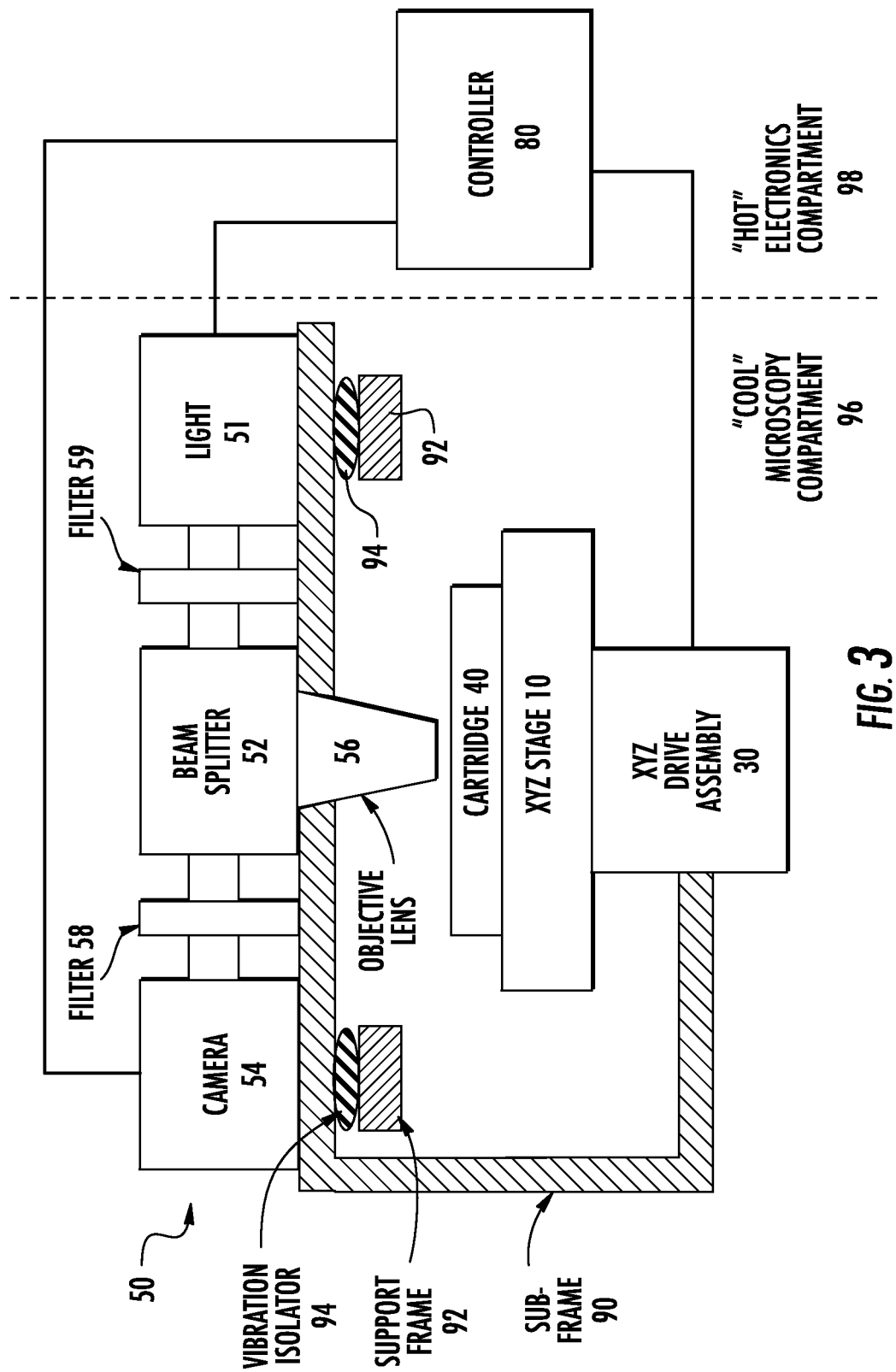
FIG. 3 is a schematic diagram of an apparatus of the present invention, showing vibration damping components and chamber separation.

FIG. 3 is a schematic diagram of an apparatus of the present invention similar to FIG. 1 above. In addition to the components shown in FIG. 1, additional features are now shown. The optical components (50) are shown as mounted on a subframe (90), which subframe is in turn mounted on a support frame (92) through vibration isolators (94). In addition, the microscopy components are shown as being contained within a separate, relatively cool, compartment (96) from the controller, which is in a relatively hot or warm compartment (98) (as compared to the microscopy compartment). The apparatus of FIG. 2 above incorporates these additional features, as discussed further below.

Figure 4:
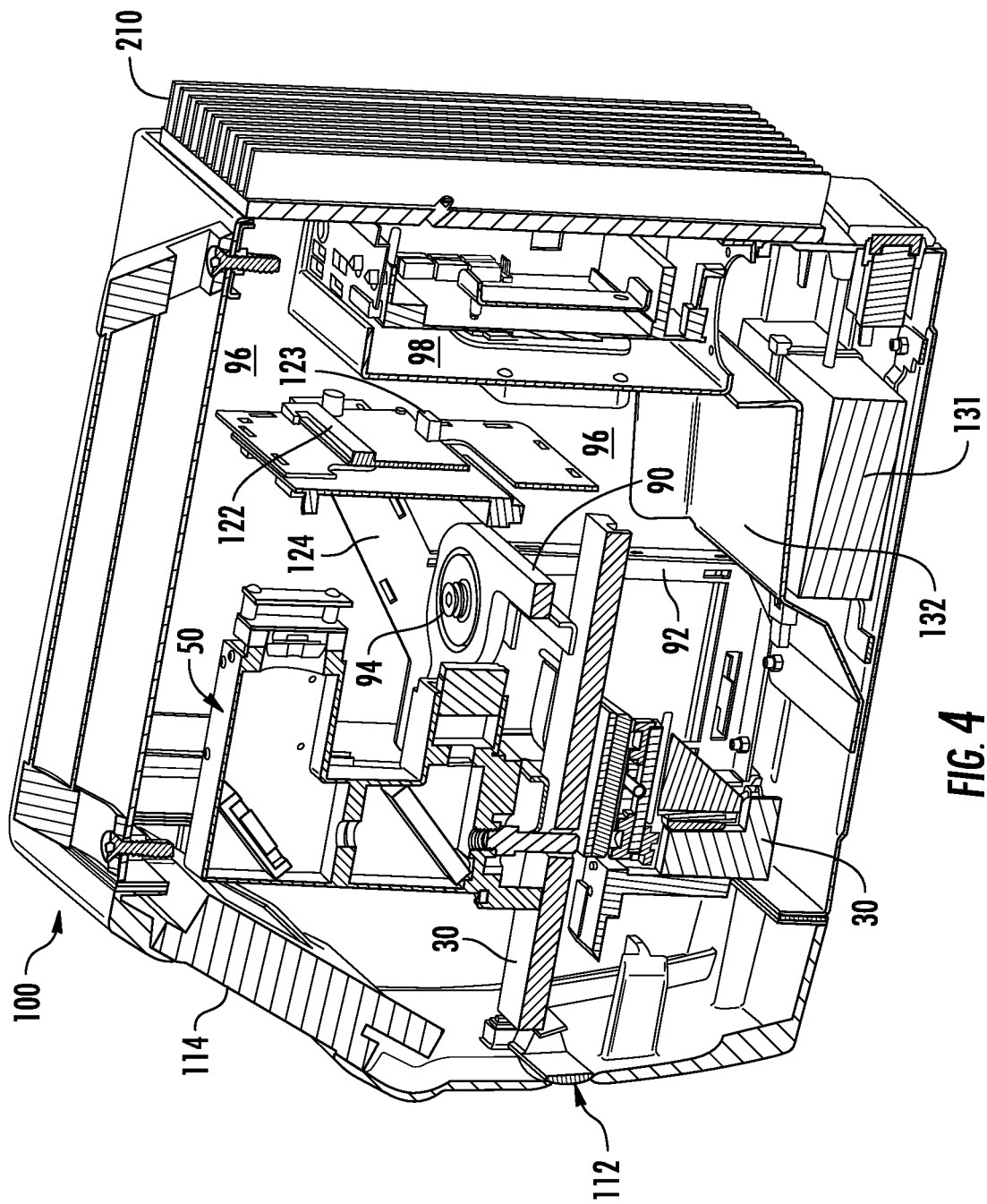
FIG. 4 is a cut-away perspective view of the apparatus of FIG. 2.

A partial cut-away perspective view of the apparatus of FIG. 2 is given in FIG. 4. A baseplate (90) serves a subframe for both the optical stage (50) and the XYZ drive assembly (30), which baseplate is in turn mounted through vibration dampening mounts (94) to the support frame (92). Any suitable active or passive vibration mount may be used, such as polymeric vibration mounts (e.g., those available from Stock Drive Products/Sterling Instruments, or any other suitable source).

An XYZ controller board (122) and a power distribution board (123) are conveniently located on a support bracket (124), which support bracket is mounted on the support frame (92), to facilitate assembly and testing of the microscopy compartment elements before they are placed into the housing, though numerous other configurations will be apparent to those skilled in the art.

A suitable power supply (131) (e.g., a fanless power supply such as MEAN WELL USP-350-12 350 W power supply) is positioned in the bottom of the unit and covered by a shield or cable tray (132) (cables not shown for clarity) to prevent tangling of cables associated with the XYZ drive assembly, image sensor, and/or light, though numerous other configurations will be apparent, including location of the power supply external to the main housing.

A heat sink (210) is mounted on the back of the apparatus to cool the electronics compartment, as discussed further below.

Figure 5:
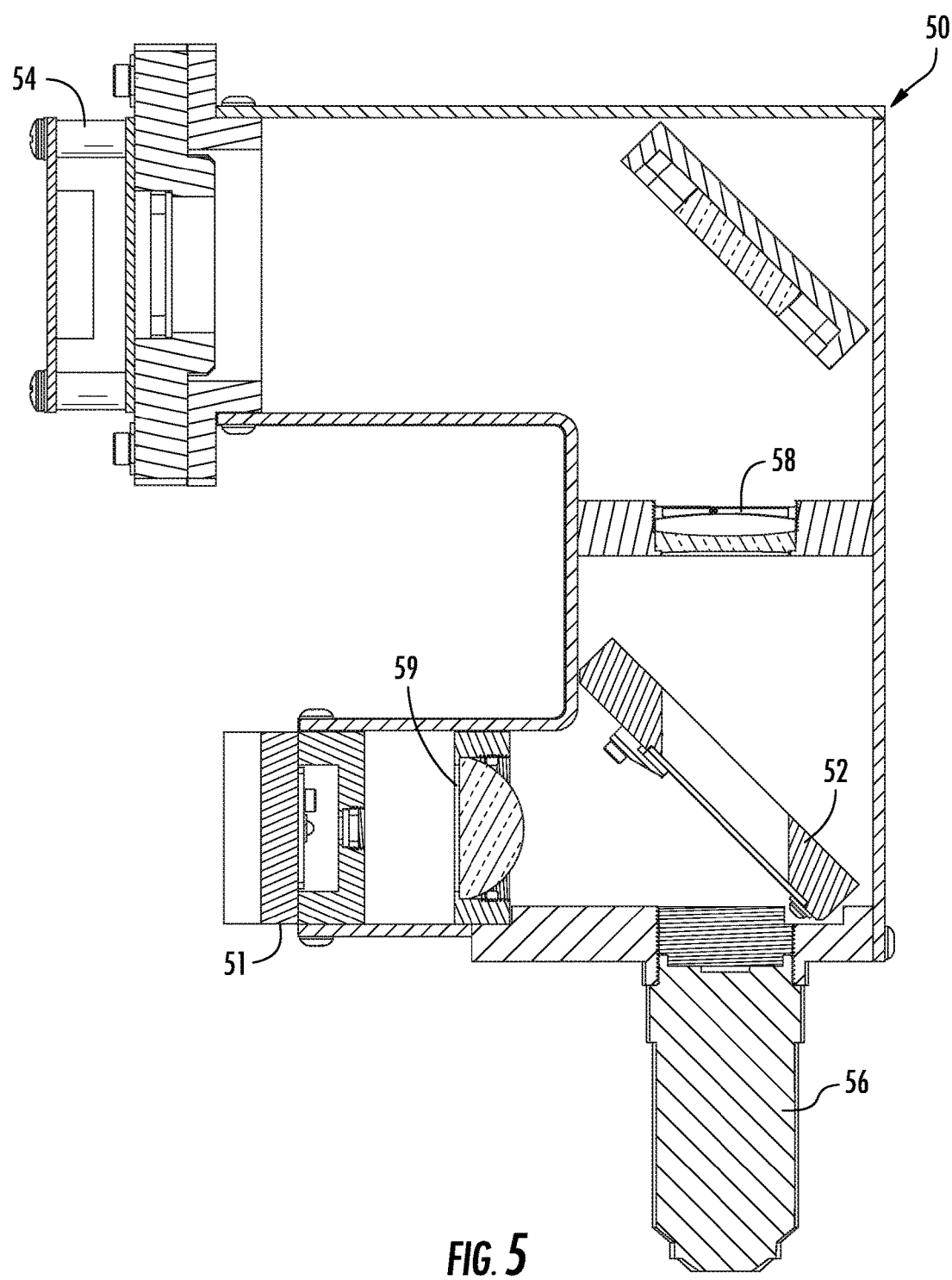
FIG. 5 is a side sectional view of an optical stage of the apparatus of FIG. 2, showing the light source, objective lens, filters, dichroic mirror and camera.

FIG. 5 is a side sectional view of an optical stage of the apparatus of FIG. 2, showing the light source, objective lens, filters including emission filters and excitation filters, dichroic mirror and image sensor (sometimes also referred to as "camera" herein), all contained within or connected to a common housing. Any suitable image sensor may be used, including CMOS image sensors, CCD image sensors, and hybrids thereof, typically 1 or 2 megapixel up to 10 or 20 megapixel, or more in resolution (e.g., a 5.0 megapixel OPTIC ANGLE image sensor). Any suitable light source may be used, including LED light (e.g. a CREE LED). Any suitable objective lens may be used, such as a 5× to 50× or 100× magnification objective lens (e.g., a NIKON MRL 00102 10× objective lens). In some embodiments, the light source is a 480 nm light source or LED; the emission filter is a dual pass filter with the center wavelength of 530 nm and 700 nm; the excitation filter has a center wave length of 470 nm, the dichroic mirror reflects 470 nm light and transmits light greater than 490 nm).

Figure 6:
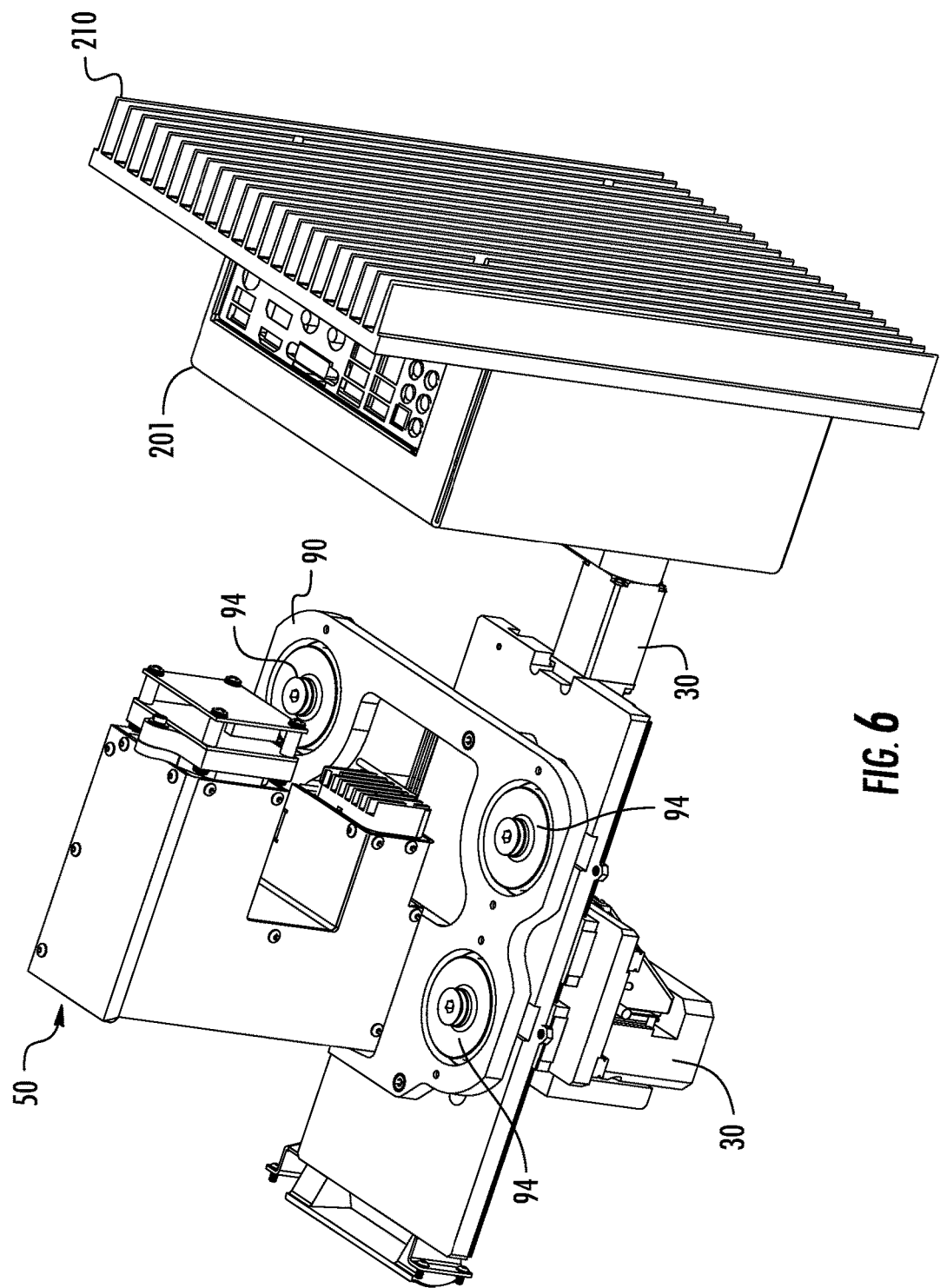
FIG. 6 is a perspective view of a microscope assembly and passively cooled microprocessor assembly of the apparatus of FIG. 2 with the cover removed and support frames removed.

The relationship of the major components of the microscopy compartment to the separate electronics compartment is shown in FIG. 6, which is a perspective view of a microscope assembly and passively cooled microprocessor assembly of the apparatus of FIG. 2 with the cover removed and support frame removed, showing the housing (201) surrounding the microprocessor board contained within the passively cooled electronics compartment. A solid state hard drive (not shown) may be conveniently mounted on the external surface of the electronics compartment housing to provide memory and storage, if desired, though again numerous other configurations will be readily apparent.

Figure 7:
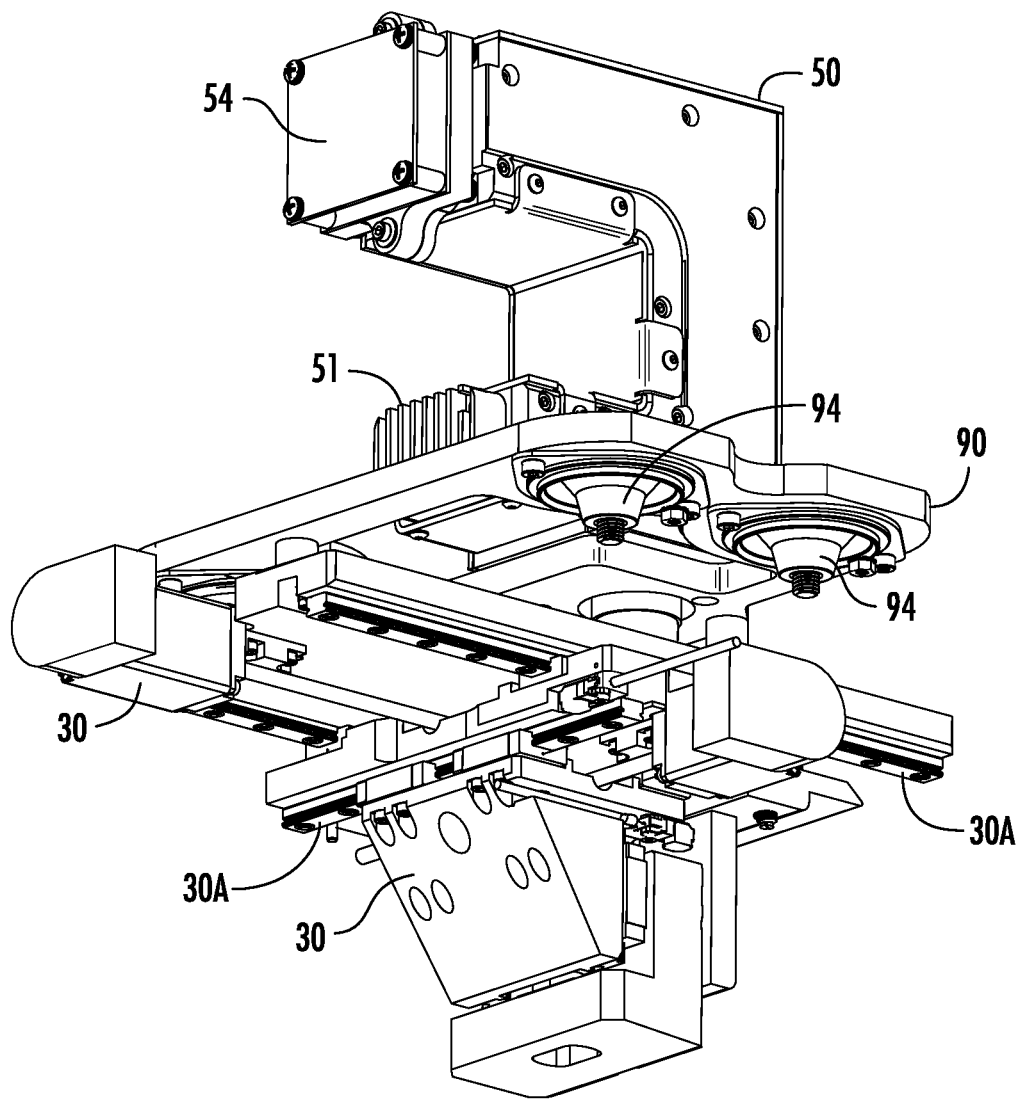
FIG. 7 is a perspective view of a microscope assembly of the apparatus of FIG. 2, with the support frame removed, showing the XYZ drive.
Figure 8:
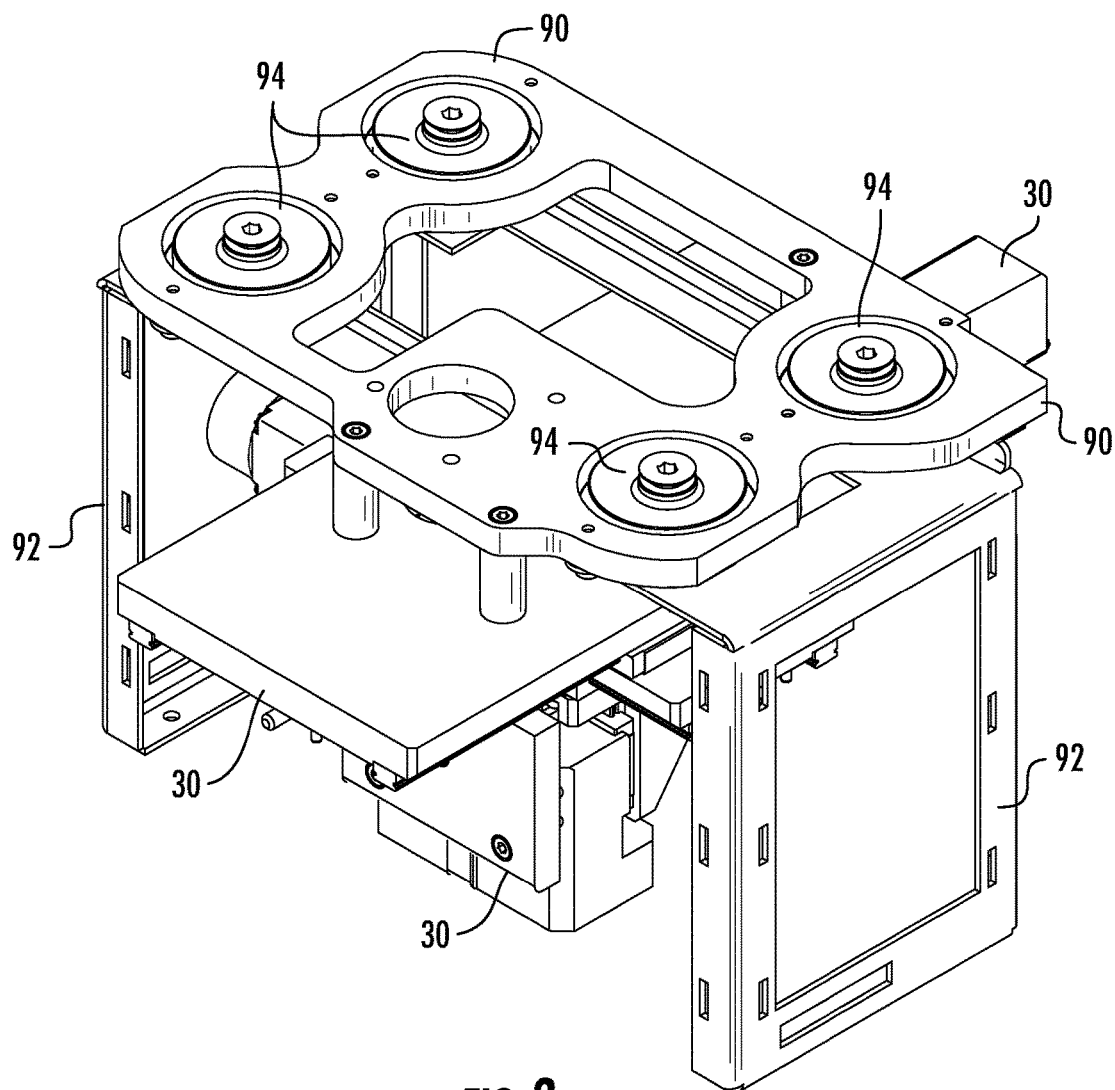
FIG. 8 is a perspective view of the mount, vibration dampers, and support frame of a microscope assembly of FIG. 2, upon which the optical stage of FIG. 5 is to be mounted.

The various components of the microscopy compartment are further illustrated in FIGS. 7-8. FIG. 7 is a lower perspective view of a microscope assembly of the apparatus of FIG. 2, showing the XYZ drive assembly (30) with linear rails (30A) mounted to the base plate (subframe (90)), the optical stage (50) mounted to the subframe (90), and the vibration isolation bushings, but with the support frame removed. Similarly, FIG. 8 is an upper perspective view of the base plate (subfame (90)), XYZ drive assembly (30) mounted on the base plate (90), mount, support frame (92) upon which the base plate (subframe (90)) is mounted through the vibration isolation bushings, but now with the optical stage (50) removed.

Figure 9:
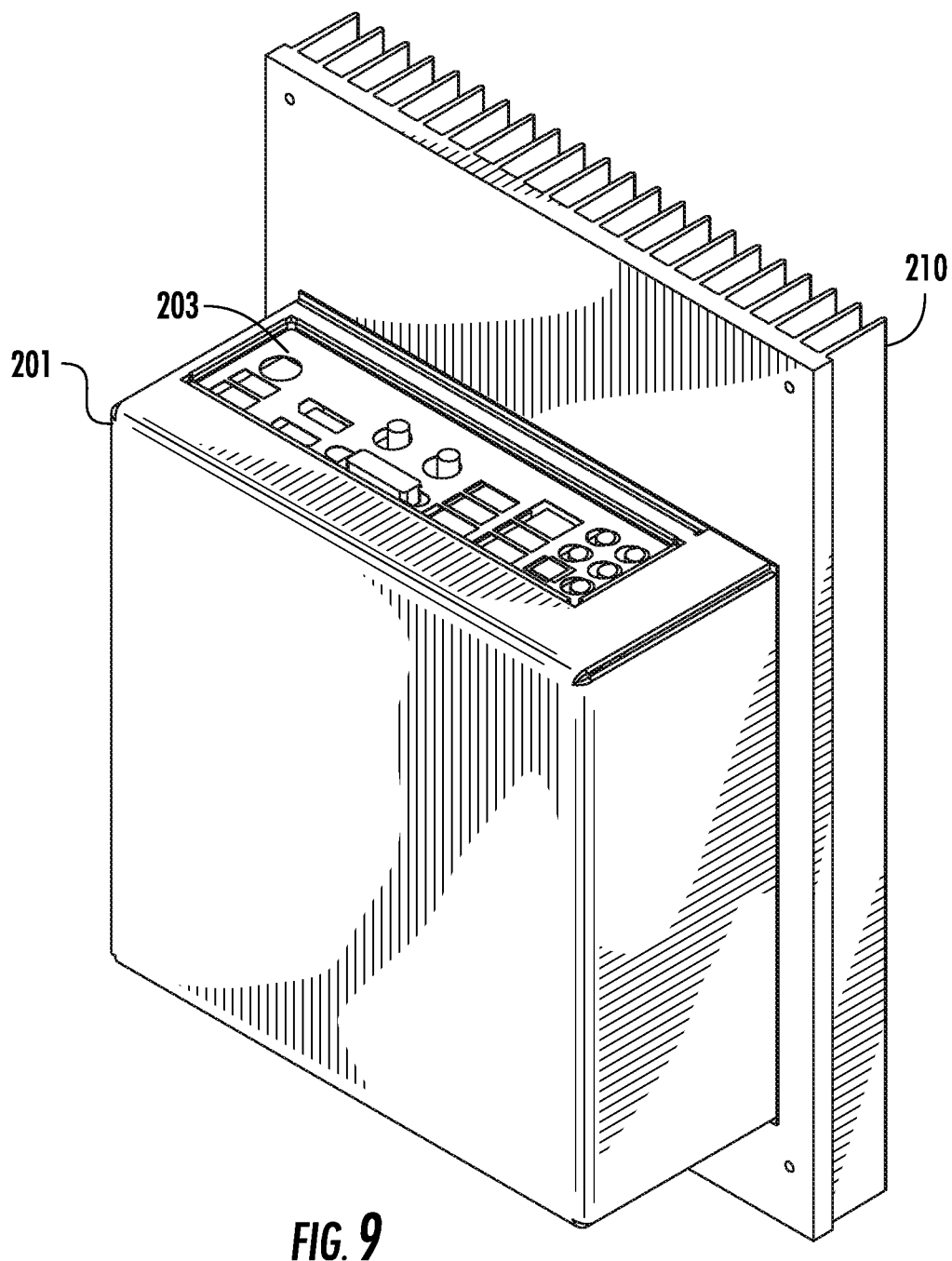
FIG. 9 is a perspective view of a passively cooled microprocessor assembly of the apparatus of FIG. 2.
Figure 10:
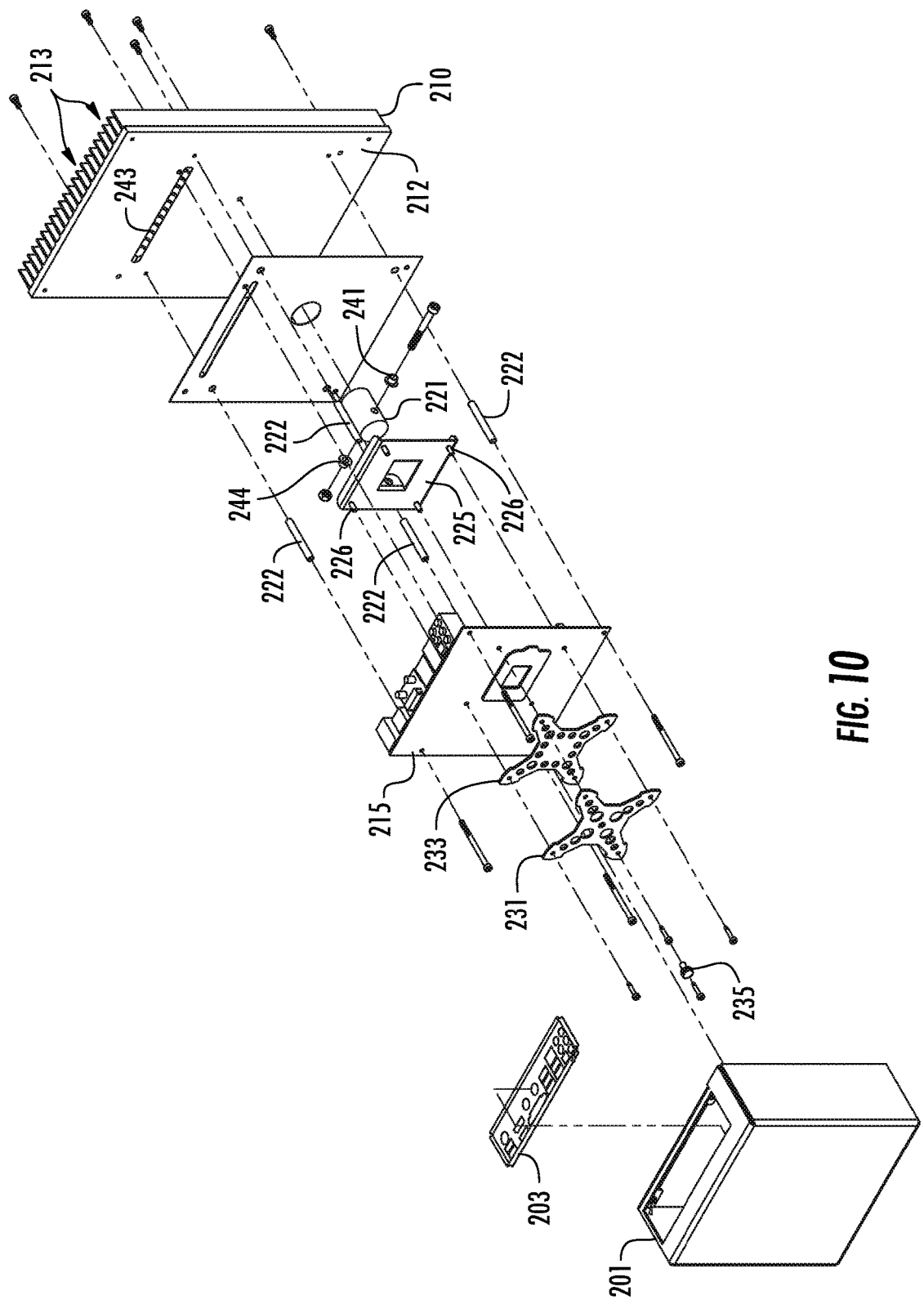
FIG. 10 is an exploded view of the microprocessor assembly of FIG. 9.
Figure 11:
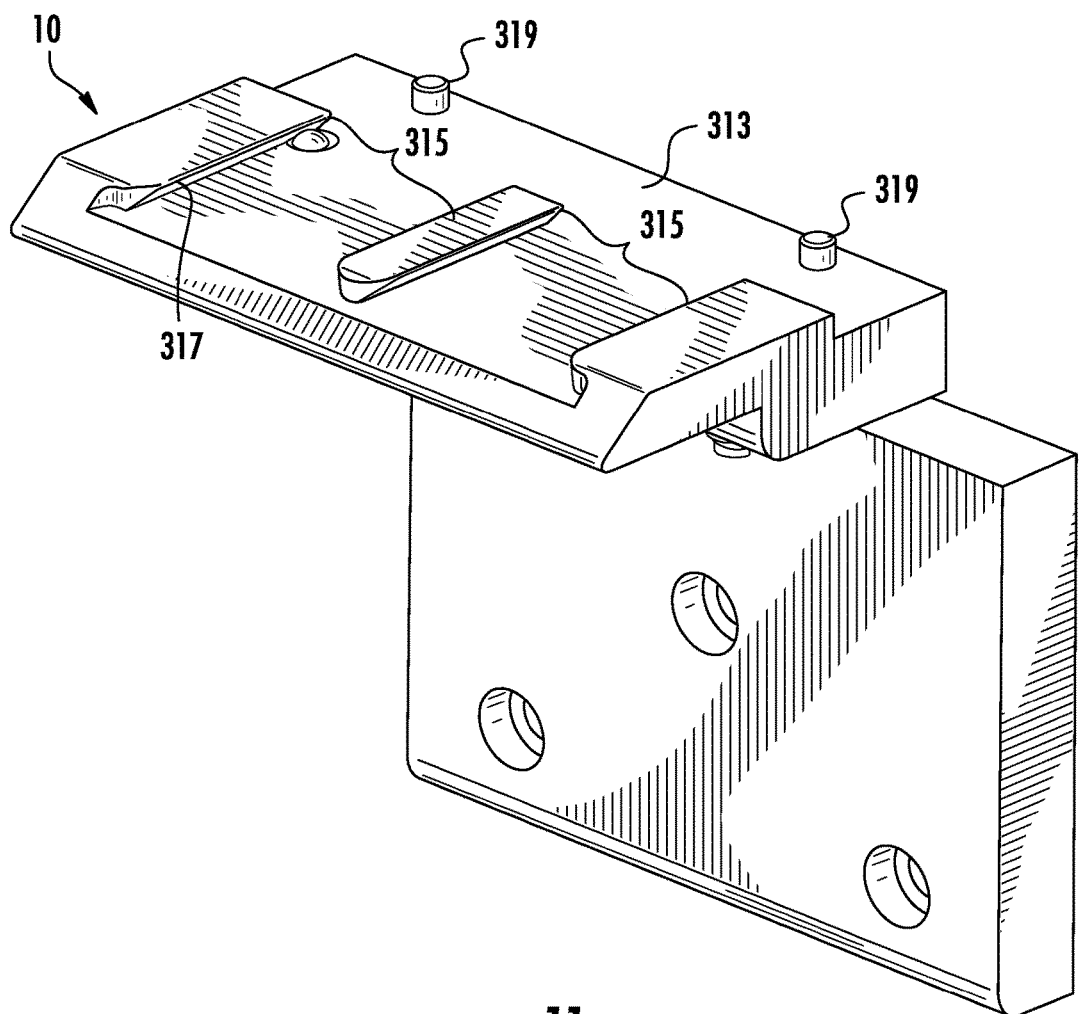
FIG. 11 is a perspective view of an XYZ stage of the apparatus of FIG. 2, as configured for retaining a pair of sample cartridges.
Figure 12:
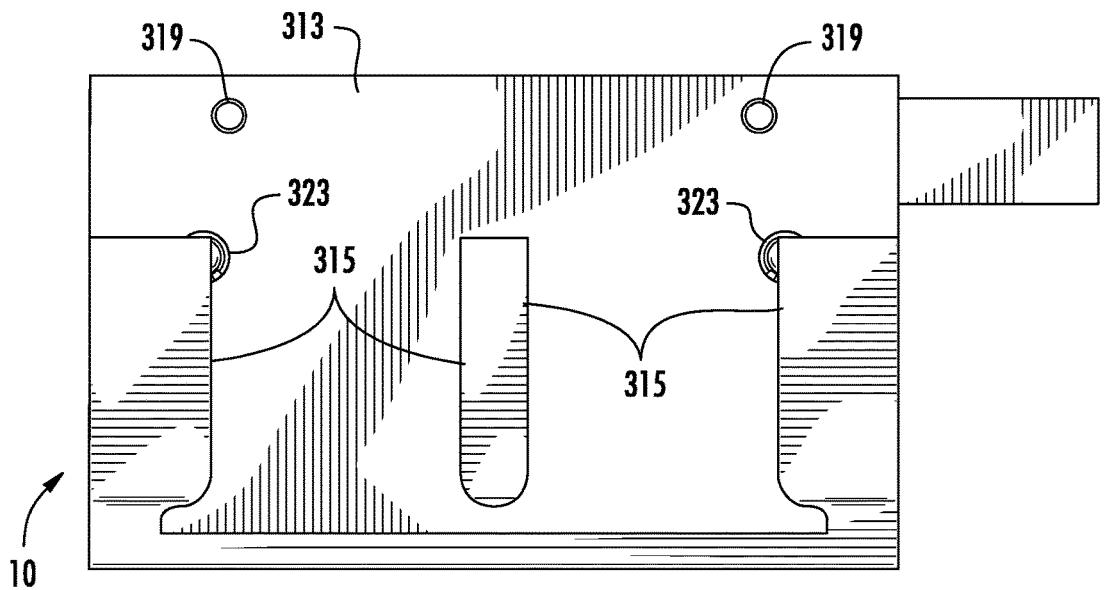
FIG. 12 is a top plan view of the XYZ stage of FIG. 11.
Figure 13:
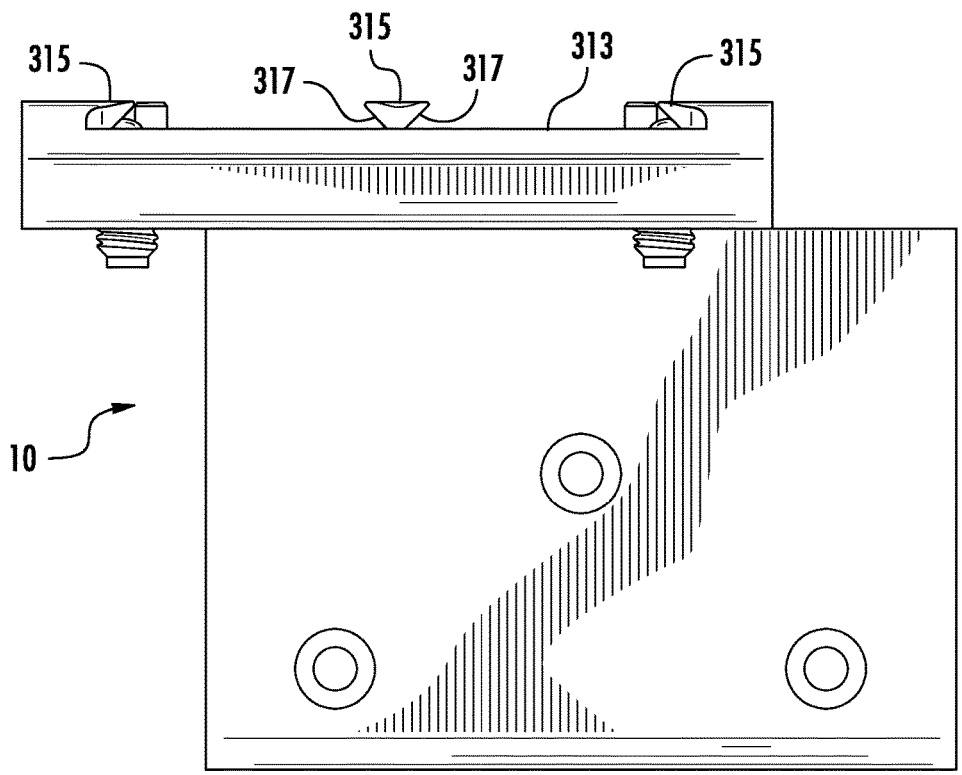
FIG. 13 is a side view of the XYZ stage of FIG. 11.
Figure 14:
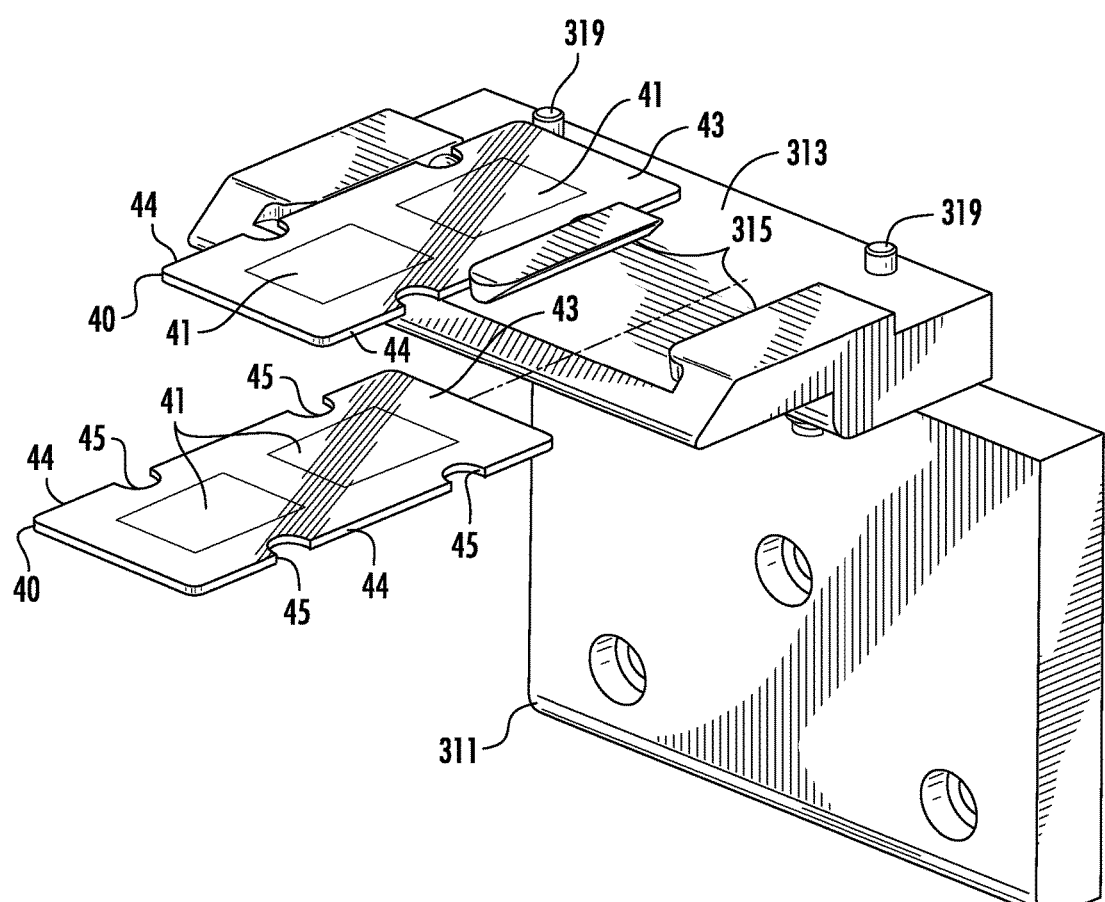
FIG. 14 is a perspective view of the XYZ stage of FIG. 11, showing a first sample cartridge seated in place, and a second sample cartridge to be inserted.

FIG. 9 is a perspective view of a passively cooled electronics compartment of the apparatus of FIG. 2, showing the electronics compartment housing (in which the microprocessor assembly is contained) mounted on the heat sink. An exploded view of this electronics compartment and microprocessor assembly is shown in FIG. 10. A mother board (e.g., a ZOTAC H67ITX-CE motherboard) is provided that carries a suitable microprocessor. Suitable microprocessors will generally be those having a thermal design power (or "TDP", sometimes also called "thermal design point") of at least 40, 50, or 60 Watts, up to 120, 140, or 160 Watts, or more. Suitable examples include, but are not limited to, Intel i7, Intel i5, and Intel i3 microprocessors.

As will be seen from FIGS. 9-10, a passively cooled microprocessor assembly includes a heat sink (210) having a front surface and back surface (212), the heat sink having cooling posts, fins or other suitable projections (213) formed on the front surface. A circuit board (215) or "mother board" having a front surface and back surface is included, with a microprocessor mounted on the circuit board front surface. A thermal coupler (221) (e.g., a copper slug or member; a heat pipe; etc.) is positioned between the microprocessor and said heat sink back surface, with the thermal coupler fixed to and in thermal contact with said heat sink back surface. A plurality of legs (222) are mounted on the heat sink back surface, with the circuit board mounted on the legs, and with the circuit board front surface spaced from and facing said heat sink back surface.

An anchor plate (225) is positioned around the microprocessor between the heat sink back surface and the circuit board front surface, with the anchor plate connected to the thermal coupler. A plurality of posts (226) are connected to the anchor plate and project through the circuit board, with a primary plate (231) connected to the posts opposite the anchor plate with the circuit board therebetween. A secondary plate (233) is slideably received on the plurality of posts and contacts said circuit board back surface. A screw (235) is threaded through the primary plate and contacts the secondary plate, so that tightening of the screw pushes the secondary plate against the circuit board back surface and clamps said microprocessor to said heat sink (optionally but preferably with a thermal grease sandwiched in between), thereby fixing the microprocessor, the thermal coupler, and the heat sink in thermal contact with one another. A housing (201) (e.g., a metal or aluminum) with an associated bezel (203) is provided around the assembly to form an electronics compartment (98) in the device separate from the microscopy compartment, as noted above. There is preferably included at least one thermal isolator (241) formed from a relatively thermally nonconductive material (e.g., an organic polymer), with the thermal coupler and the anchor plate are connected to one another through the at least one thermal isolator.

A ventilation opening (243) such as an elongated slot may optionally be formed in the heat sink to further facilitate cooling of the electronics chamber. Such an opening or port is preferably configured to inhibit or slow the progression of liquid or solid particles from outside the apparatus entering into the electronics chamber, such as by configuring the slot at a downward angle.

FIGS. 11 to 14 illustrate a first embodiment of an XYZ stage (10) of the apparatus of FIG. 2, as configured for retaining a pair of sample cartridges (40). As illustrated, each sample cartridge contains a pair of separate chambers (41), and the sample cartridges are reversibly insertable into the XYZ stage. One or both of the chambers may optionally contain exogenous targets to facilitate autofocus, as described below.

As shown in FIGS. 11 to 14, such a stage is configured to receive a sample cartridge having an end portion (43), a pair of generally parallel opposing side edge portions (44), and a locking edge portion formed (45) thereon, with each of said side edge portions having an upper corner portion, and with said locking edge portion positioned at an angle in relation to both said side portions and said front portion. The XYZ stage itself comprises a base member (311) having a planar stage surface portion (313), and a pair of generally parallel oppositely facing guide members (315) on said planar stage surface, each of said guide members having an inwardly angled edge portion (317) configured for contacting one of the cartridge side edge upper corner portions when the sample cartridge is inserted therebetween. A terminal block member (319) is provided on the planar stage surface portion and positioned to contact the sample cartridge end portion when the sample cartridge is inserted between said guide members. A locking member (323) (e.g., a spring-loaded ball detent) is included on the planar stage surface portion and positioned to press against the sample cartridge locking edge portion when the sample cartridge is inserted between the guide members and in contact with said terminal block, so that pressure is exerted by said lock member through said sample cartridge against both said terminal block and one of said guide members, whereby the cartridge is removably locked in place on the XYZ stage in at least the Z plane of movement, preferably all three of the X, Y and Z planes of movement, and still more preferably with the cartridge secured with reference to, or with respect to, the X, Y, and Z axes of rotation as well.

Figure 15:
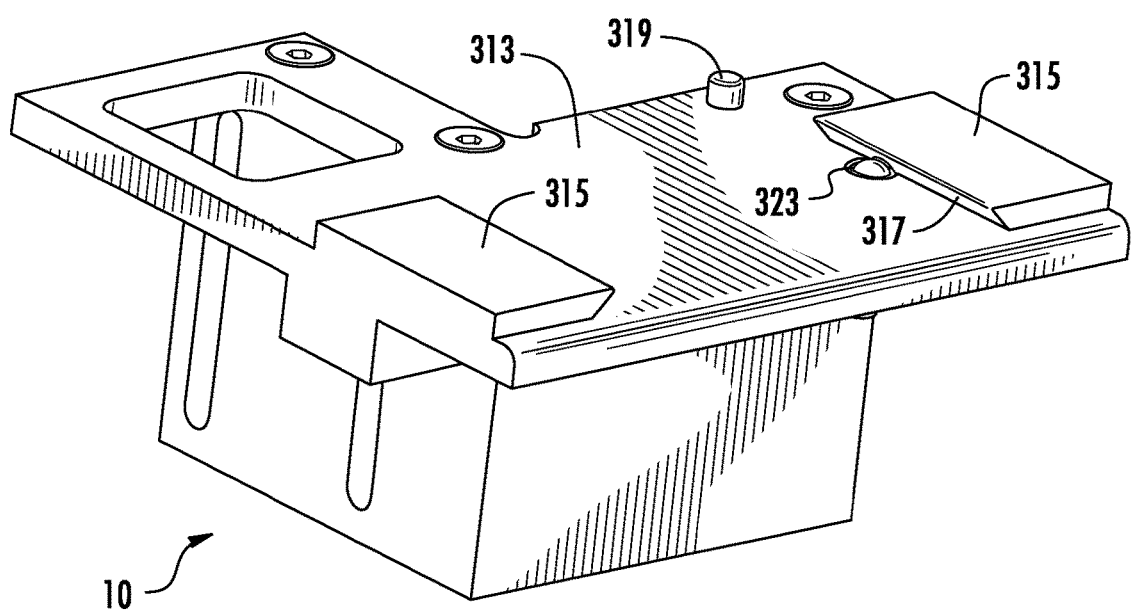
FIG. 15 is a perspective view of an alternate XYZ stage for an apparatus of FIG. 2, in which a single sample cartridge is to be inserted.
Figure 16:
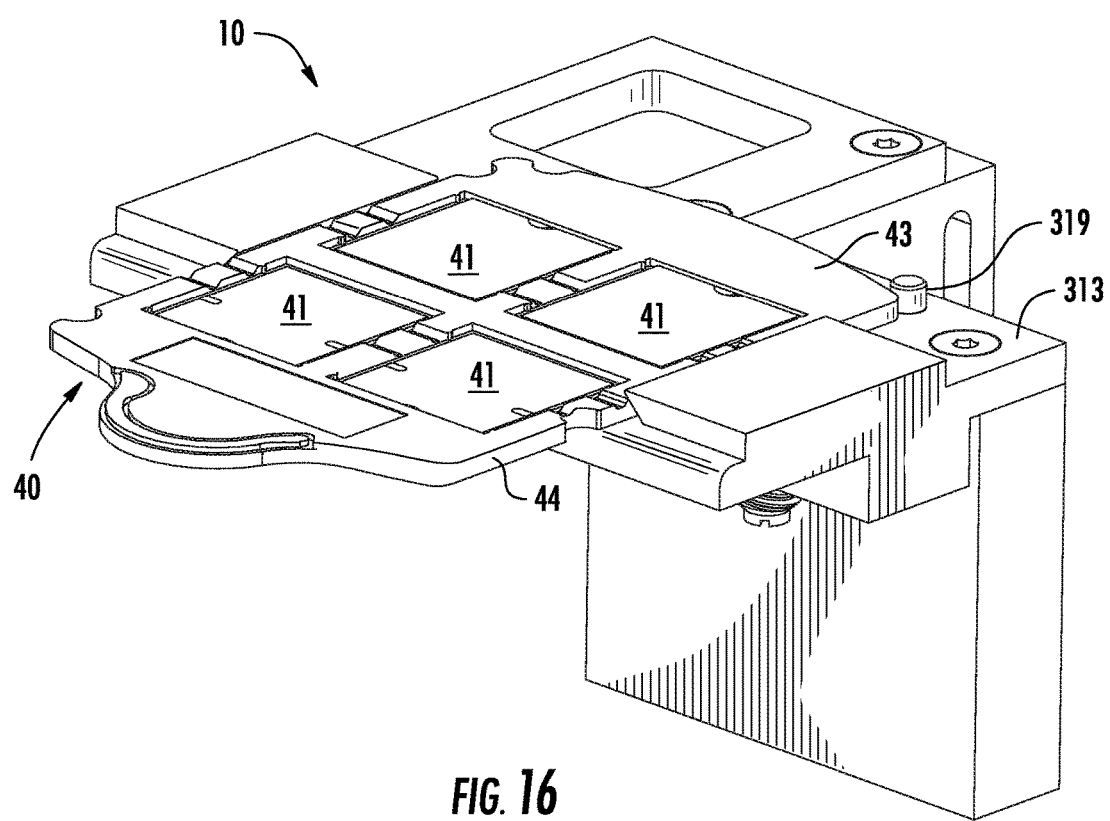
FIG. 16 is a perspective view of the XYZ stage of FIG. 15, with a sample cartridge inserted.

FIGS. 15 to 16 illustrate a second embodiment of an XYZ stage (10) of an apparatus of FIG. 2, as configured for retaining a single sample cartridge (40). Like components as compared found in FIGS. 11 to 14 are assigned like numbers. As illustrated in FIGS. 15-16, the sample cartridge contains four separate chambers (41) (sometimes also referred to as "quadrants" or "quads"), each of which may (for example) be used to contain a milk, colostrum or secretions sample from a separate one of each of the four teats of a cow's udder. One, some, or all of the chambers may optionally contain exogenous targets to facilitate autofocus, as described below. As illustrated, the sample cartridge is nonreversible, or is configured so that it may be inserted into the XYZ stage in a single orientation only. When each teat of origin of a milk sample deposited within each chamber is identified or recorded, this facilitates identification of an infected teat or gland for subsequent treatment, and/or aids in identifying the severity or extent of infection of a particular cow.

Figure 17:
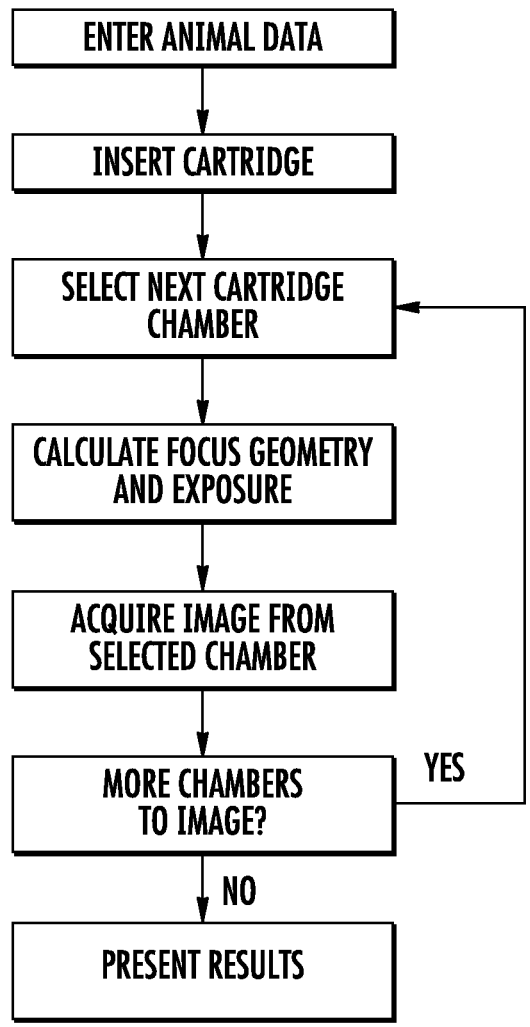
FIG. 17 is a schematic flow chart of a first mode of operation of an apparatus of FIG. 2 for detecting mastitis in cattle.

FIG. 17 illustrate a mode of operating a device as described above, with FIGS. 18-23 illustrating the images displayed on (i.e., "screen shots" from) the user interface or "touch screen" of the apparatus of FIG. 2 described above. All components including the XYZ drive assembly, the light, the camera or imaging device, and the touch screen, may be operatively associated with and controlled by the controller or microprocessor as discussed above, programmed in a suitable language such as MICROSOFT C#.

Figure 18:
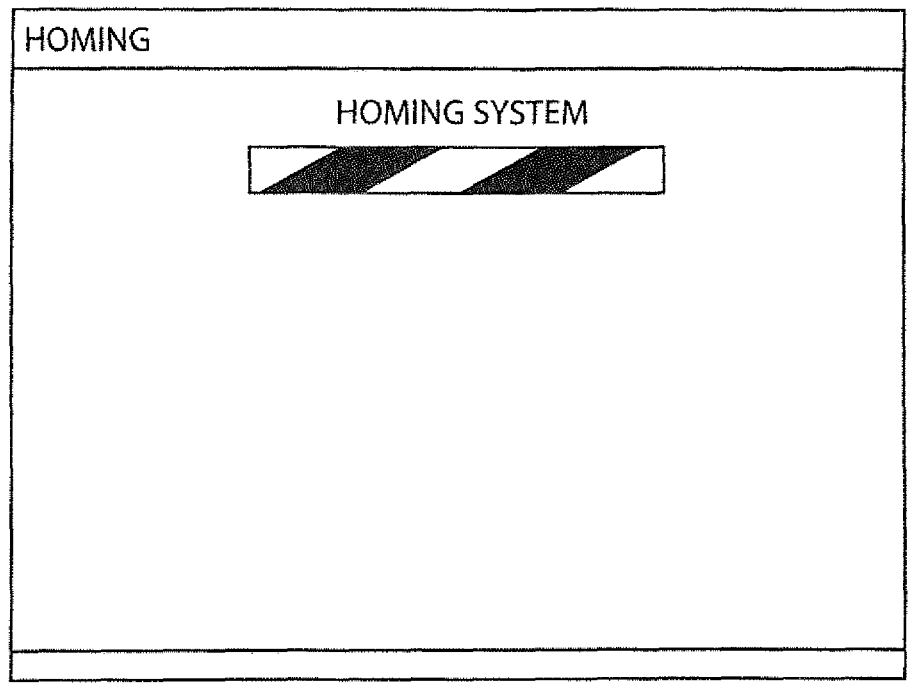
FIG. 18 illustrates the display of a user interface of an apparatus of FIG. 2 during homing of the optical stage.

Upon activating the system, the XYZ stage can be "homed" in accordance with known techniques, such as with electromechanical sensors, during which time a "homing" message such as shown in FIG. 18 may be displayed on the display screen.

Figure 19:
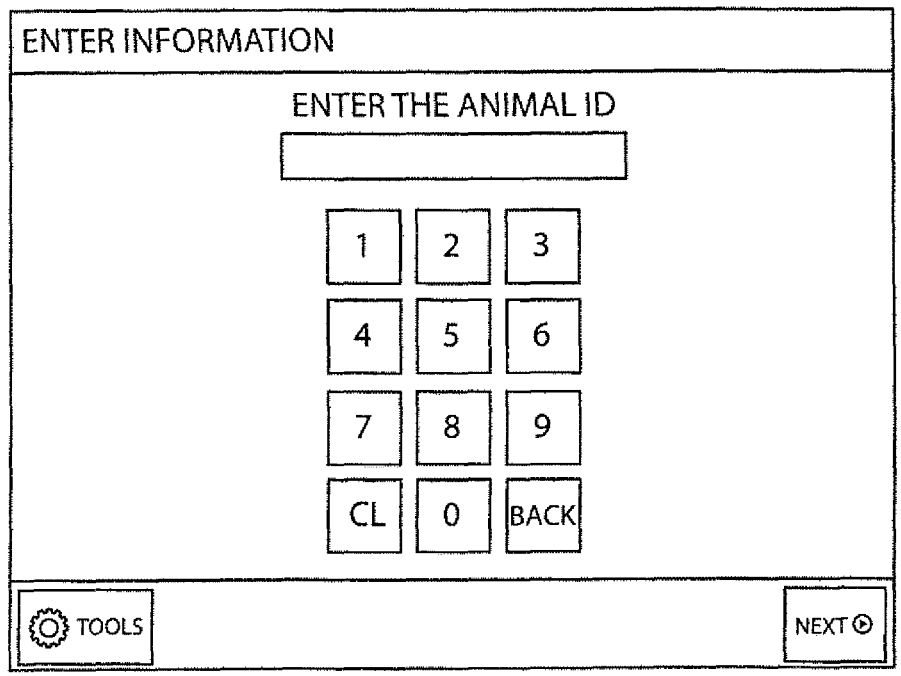
FIG. 19 illustrates the display of a user interface of an apparatus of FIG. 2 for input of animal data or information, particularly the identity of the animal from which the sample(s) are collected.
Figures 20, 21:
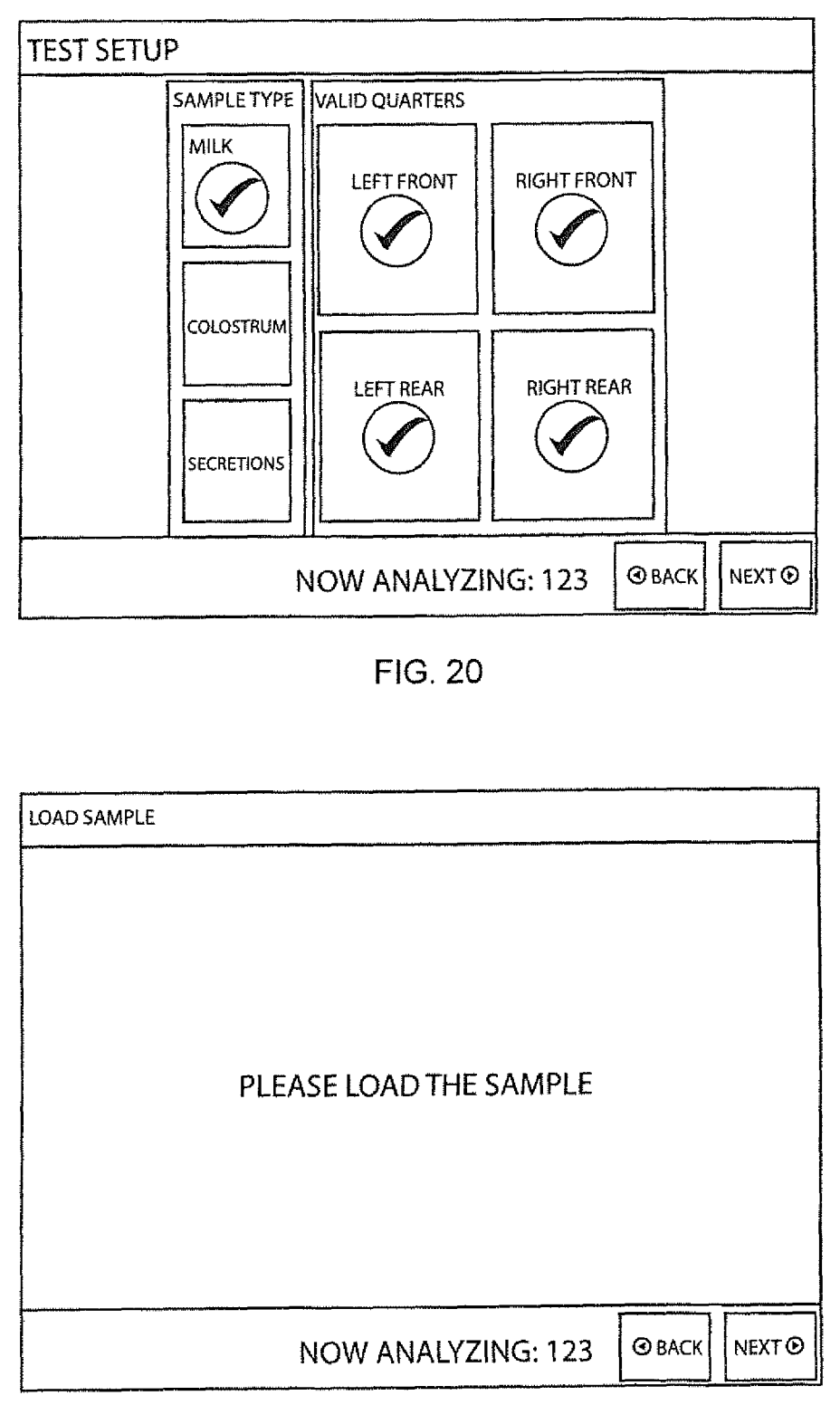

As shown in FIG. 17, following the process may begin (before or after "homing") by entering animal data, such as an animal identification or "ID" through a display interface such as shown in FIG. 19. Before or after animal identification is entered, the type of sample to be screened may be selected (e.g., milk, colostrum, secretions), and/or the number of separate chambers to be analyzed can be entered (which, in the case of a cow, can correspond to the quadrant of the mammary gland, and/or the specific teat, from which the sample is collected), such as through a suitable display and data entry screen such as shown in FIG. 20. Elimination of one or more chambers from the analysis procedure may advantageously reduce the overall time of the test.

The sample cartridge may be inserted (before or after the entry of the animal data), optionally as prompted through the display of a "load sample" or "load cartridge" message such as given in FIG. 21. If desired, access to the cartridge carrier may be secured through a manually operated door, or an automated door controlled by the controller to open, and close, at the appropriate time in the operating cycle.

After the sample cartridge is inserted, the microscope is autofocused on the first sample chamber (as shown in FIG. 17) and imaging (including identification and counting of cells of interest) is carried out on the first sample chamber. Autofocusing may be carried out by any suitable technique, including but not limited to those described in U.S. Pat. Nos. 8,014,583; 7,141,773; 5,790,710; 5,647,025; 5,483,055; and 4,810,869, and variations thereof that will be apparent to those skilled in the art. In some embodiments, autofocusing is carried out prior to acquisition of an image of the specimen or sample through the camera, typically through calculating a focus score. The focus score can be calculated by any suitable technique, including but not limited to those described in F. Groen et al., *A comparison of different focus functions for use in autofocus algorithms*, Cytometry 6, 81-91 (1985). Difference from the background, given a uniform background, can be calculated a number of ways, including but not limited to differences in contrast, gradient, and variance.

Figure 22:
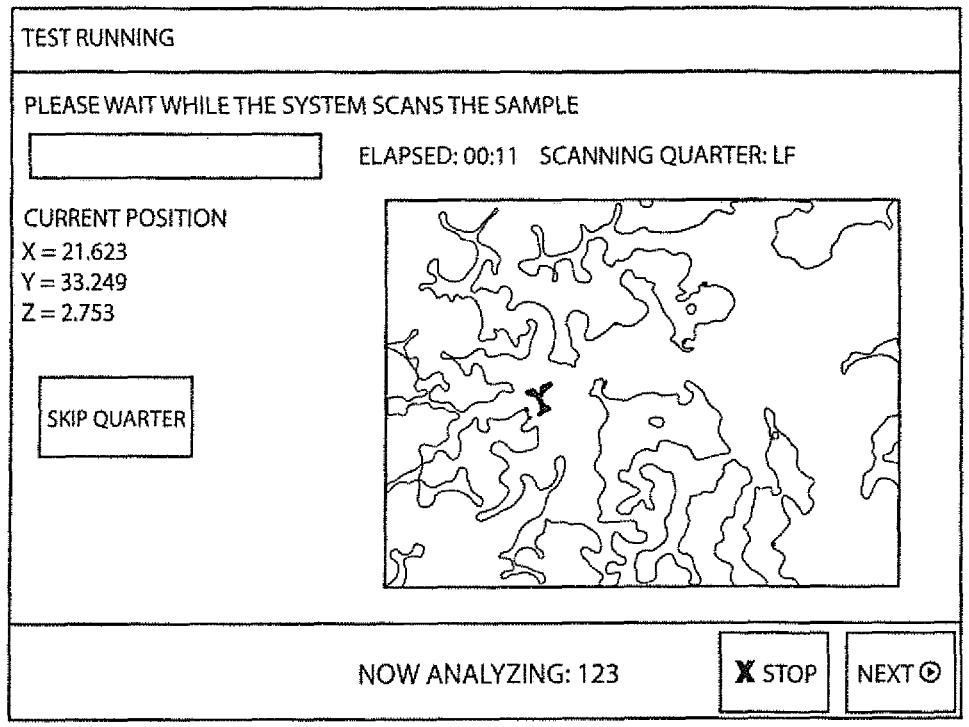
FIG. 22 illustrates the display of a user interface of an apparatus of FIG. 2 during image acquisition and analysis of one of the four separate chambers of a sample cartridge.

A display such as shown in FIG. 22 may optionally be provided during imaging, giving information such as the microscope image and the position (XY, and optionally Z) being scanned or imaged. Once imaging of the first chamber is completed, the optical stage is positioned by the controller over the next sample chamber to be imaged, again autofocused thereon as described above, and again imaged as described above. This process is repeated until all sample chambers have been imaged. In the alternative, an input signal can be provided to the controller to omit sampling of a particular chamber, such as through the touch screen 115, for example by selecting individual "valid quarters" through the "left front", "right front", "left rear", and "right rear" buttons of the screen shown in FIG. 20, and/or by a "skip quarter" button as shown in FIG. 22.

Identification and counting of cells can be carried out in accordance with known techniques or variations thereof that will be apparent to those skilled in the art. See, e.g., A. Katz, *Image Analysis and Supervised Learning in the Automated Differentiation of White Blood Cells from Microscopic Images*, Master's Thesis (Royal Melbourne Institute of Technology 2000); see also U.S. Pat. No. 7,991,213 to Tafas and US Patent Application Nos. 2004/0085443 to Kallioniemi; 2011/0182490 to Hoyt; 2011/0255753 to Levenson; and 2011/0255745 to Hodder.

Determination of infection can be carried out from cell counts and identities in accordance with known techniques or variations thereof that will be apparent to those skilled in the art, such as by total leukocyte count or differential leukocyte count. See, e.g., Rodriguez and Galanaugh, supra; H. Tvedten et al., Automated differential leukocyte count in horses, cattle, and cats using the Technicon H-1E hematology system, *Vet. Clin Pathol.* 25, 14-22 (1996); G. Lehner et al., Milk leucocyte population patterns in bovine udder infection of different aetiology, *J. Vet. Med. B. Infect Dis. Vet. Public Health* 47, 581-89 (2000); H. Dosogne et al., Differential Leukocyte Count Method for Bovine Low Somatic Cell Count Milk, *J. Dairy Sci.* 86, 828-834 (2003); M. Albenzio et al., Differential Leukocyte Count for Ewe Milk with Low and High Somatic Cell Count, *J. Dairy Research* 78, 43-48 (2011).

Figure 23:
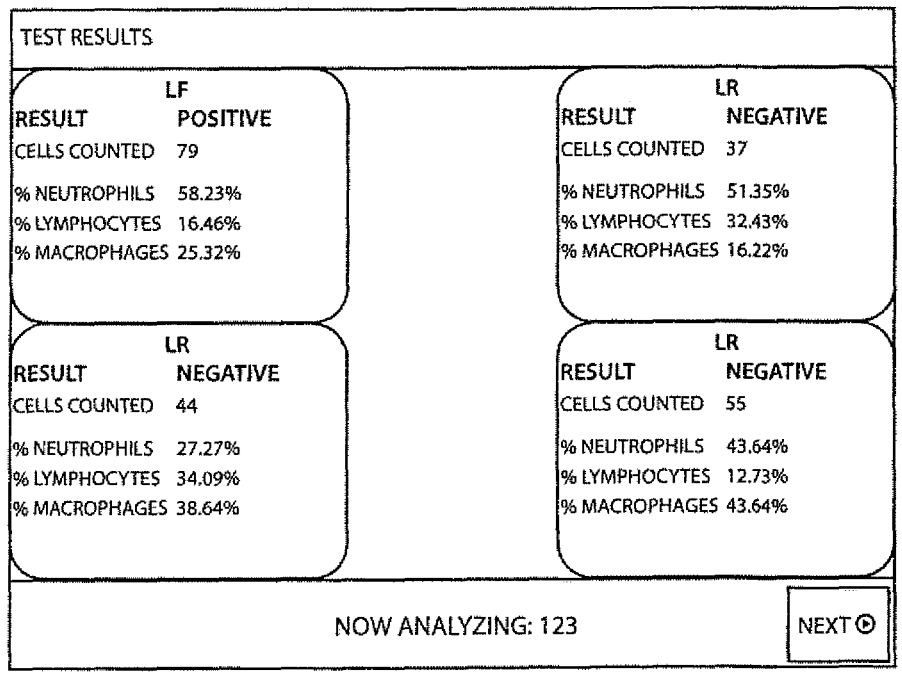
FIG. 23 illustrates the display of a user interface of an apparatus of FIG. 2 after image acquisition and differential leukocyte analysis has been completed. Note that one of the four quarters is indicated as "positive" for mastitis.

Results of imaging, identification, counting and analysis can be printed, stored on a suitable memory, and/or displayed on a final image screen such as that shown in FIG. 23.

Exogeneous Targets.

General considerations for selecting the exogeneous target are as follows: The exogeneous target should be visible by the particular optical system in use. This will depend on the magnification, excitation wavelength, size of field of view, etc. This will influence decisions on which size, shape, emission wavlengths, etc. of the texture. In addition, the exogeneous target should be distinguishable from the target objects. Preferably, the The exogeneous target reside at substantially the same (or a known distance from) the focal plane of the target objects (e.g., be mixed with a biological sample suspected of containing cells to be imaged and/or counted, and/or placed in the same chamber as will contain a biological sample comprising cells to be imaged and/or counted). The exogeneous target should be of a size, shape, and number so as to not substantially obscure the view of the intended target objects, such as cells to be imaged and/or counted. And, the exogeneous target should provide sufficient contrast with an empty field of view so as to provide an adequate focal peak and allow for reliable, reasonably rapid, and/or robust focusing.

The exogenous targets may be formed of any suitable material, including organic polymers, inorganic materials (including crystalline materials, amorphous materials, metals, etc.) and composites thereof.

The exogenous targets may be contained loosely within the chamber, fixed to one wall of the chamber, or surface to be imaged (e.g., by adhesive, by electrostatic, hydrophilic, or hydrophobic interaction, covalent bond directly or through a linking group, etc.), and/or formed on one wall of the chamber (e.g., by molding, etching, painting, silk-screening, lithography, etc.).

The exogenous targets may be opaque or transparent. When transparent the targets may be "tinted" so as to transmit light therethrough at a predetermined wavelength (for example, so that they appear red, green, blue, yellow, etc., to a human observer).

The exogenous targets may be regular or irregular in shape (for example, cylinders, spheres, cubes, pyramids, prisms, cones, rods, etc.). In some embodiments, the targets have an average diameter of from 0.1, 0.5 or 1 micrometers up to 2, 5, or 10 micrometers.

The number of exogenous targets is not critical, but in some embodiments the speed of the autofocus process can be increased by increasing, at least to a point, the number of exogenous targets in the chamber so that the targets are readily located in the automated microscope. Where a plurality of targets are included in the sample chamber (e.g., 2, 4, 6, 8 or 10 targets, up to 100, 200, 400, 600 or 800 exogenous targets, or more), in some embodiments that plurality preferably consists of or consists essentially of targets having substantially the same size, shape, and optical characteristics.

In some embodiments, the targets are beads, such as fluorescent microbeads. Such microbeads are commonly available and used for calibrating flow cytometers or fluorescent microscopes (see, e.g., U.S. Pat. Nos. 4,698,262; 4,714,682; and 4,868,126).

The targets are preferably optically distinguishable from cells to be counted (and hence would not be useful as calibration standards for the particular cells to be counted and/or imaged by the methods described herein). Optically distinguishable may be achieved by any suitable technique, such as by utilizing targets of a different and distinguishable shape from the cells to be counted, by utilizing targets that emit, transmit, and/or reflect light at a different wavelength from the cells to be counted when under the same illumination conditions, and combinations thereof.

Selected aspects of the present invention are explained in greater detail in the following non-limiting Examples.

Example 1

Exogeneous Target-Assisted Autofocus

An embodiment of the invention is carried out by addition of microscopic fluorescent beads to a sample to be imaged, in combination with an automated microscope including an XYZ stage under the control of a computer. A sufficient concentration of such beads will ensure that there is a very high probability of having beads within any given field of view, thereby ensuring that there is sufficient texture for the autofocus algorithm.

In general, when an automated microscope focuses, a typical approach is a sequence as follows:
1. Move to some Z location.
2. Mathematically process the digital image to obtain a "score" of the image that represents, in relative terms, whether the field of view is in focus.
3. Repeat steps 1 and 2 until a peak is found in the focus graph. This peak will represent the position at which that field of view is in best focus.

Example 2

Sample or Surface Interpolation

By including exogeneous focal targets at a plurality of separate locations in the sample to be imaged, or on the sample carrier surface to be imaged (so long as cells/analytes to be imaged and focus particles are in the same image plane or "Z stack"), the surface or sample can be interpolated by inclusion of a suitable interpolation program, routine or subroutine within the autofocus subroutine, to thereby facilitate imaging of the sample, or speed imaging of the sample.

Such interpolation can be carried out by any suitable algorithm or method, including but not limited to the planar best fit method, the weighted least squares fit method, and the quadratic fit method. Such procedures are known and described in, for example, I. Coope, "Circle fitting by linear and nonlinear least squares". *Journal of Optimization Theory and Applications* 76 (2): 381 (1993); Ake Bjorck, *Numerical Methods for Least Squares Problems*, Society for Industrial and Applied Mathematics (April 1996); etc.

The planar best fit method is illustrated by the equation:

$$z = Ax + By + C$$

Method 1 involves the average of x, y and z points; Method 2: Least Squares Linear Regression; and Method 3: Weighted Least Squares Regression. Data: x, y, and z focus points collected outside the viewing/imaging sample area. At least 3 data points are required.

The quadratic fit method is illustrated by the equation:

$$z = Ax^2 + By^2 + Cxy + Dx + Ey + F.$$

The method involves a second order quadratic surface. Data: x, y, and z focus points are collected somewhere outside the viewing/imaging/sample area. At least six data points are required.

When the cells to be imaged are collected and imaged within the same enclosed chamber, the exogeneous targets may be simply included in the chamber. When cells to be imaged are captured by antibodies bound to a carrier surface, the sample is collected on a surface that carry antibodies that bind the cells. Antibodies may be covalently or non-covalently coupled to the surface by any suitable technique as is known in the art.

To carry out interpolation, it is preferable that the exogenous targets be in or on the chamber, or on the (generally planar, but not always perfectly planar) surface supporting the specimen or sample to be imaged, at a plurality of locations. While in some embodiments 3 locations will be sufficient, in other embodiments 4, 5, or 6 or more locations are desired. The locations may be separate and discrete from one another (that is, without exogenous target deposited therebetween) or may be contiguous (that is, with exogenous target therebetween). Spacing between the locations will in general be determined by factors such as magnification and the size of the sample to be imaged (particularly in the XY dimensions), but in some embodiments the locations will be spaced apart at least 10, 20, or 30 percent of the average width of the sample support surface or chamber to be imaged. Such spacing may be achieved by depositing the exogenous targets at discrete locations around the region where the antibodies are deposited, by depositing the exogenous targets at discrete locations among the region where the antibodies are deposited, by depositing exogenous targets on at least a major portion, or all of, the support surface or chamber to be imaged, etc.

The foregoing is illustrative of the present invention, and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

We claim:

1. A microscope assembly for use in an automated portable microscope apparatus, comprising: a support frame; a subframe; a plurality of vibration isolators mounted between said support frame and said subframe such that said plurality of vibration isolators are configured to vibrationally isolate said subframe from said support frame; an XYZ stage configured to support a sample cartridge, the XYZ stage being mounted at a first mounting position on the subframe; an optical unit mounted on the subframe at a second mounting position, the optical unit being configured to support microscope optical components, and wherein the first mounting position is spaced apart from the second mounting position; and an XYZ drive interconnecting said XYZ stage to said subframe, wherein the XYZ drive is rigidly mounted to the subframe, wherein said XYZ drive comprises a plurality of linear rails mounted to said subframe and said XYZ stage.

2. The microscope assembly of claim 1, said XYZ stage configured to receive a sample cartridge having an end portion, a pair of generally parallel opposing side edge portions, and a locking edge portion formed thereon; said XYZ stage comprising:
    a base member having a planar stage surface portion;
    a pair of generally parallel oppositely facing guide members on said planar stage surface and configured for slideably receiving said cartridge therebetween;
    a locking member on said planar stage surface portion and positioned to press against the sample cartridge locking edge portion when said sample cartridge is inserted between said guide members, so that pressure is exerted by said lock member through said sample cartridge against at least one of said guide members, whereby the cartridge is removably locked in place on the XYZ stage in the Z plane.

3. The microscope assembly of claim 1, wherein the XYZ stage is configured to receive a sample cartridge that is removably inserted into or engaged by the XYZ stage.

4. The microscope assembly of claim 1, further comprising optical components mounted on the subframe.

5. The microscope assembly of claim 4, wherein the optical components comprise a light source, a beam splitter, a camera and an objective lens that are configured so that light from the light source is directed onto the sample cartridge and light emitted or fluoresced from the sample cartridge is directed to the camera.

6. The microscope assembly of claim 5, wherein the optical components further comprises filters provided between the camera and beam splitter and between the light source and beam splitter, the filters being configured to filter wavelengths of light that are directed to the sample cartridge and to filter wavelengths of light that are directed to the camera, respectively.

7. The microscope assembly of claim 6, further comprising a controller configured to control one or more of the optical components and the XYZ drive assembly.

8. The microscope assembly of claim 1, wherein the plurality of vibration isolators define opposing first and second sides, wherein the XYZ stage is on the first side and the optical unit is on the second side and the XYZ stage is rigidly connected to the optical unit.

9. The microscope assembly of claim 8, wherein the subframe extends between the first and second sides defined by the plurality of vibration isolators.

10. The microscope assembly of claim 1, wherein said plurality of vibration isolators comprise a plurality of annular vibration isolators.

* * * * *